US011517587B2

(12) United States Patent
Ehrlich et al.

(10) Patent No.: US 11,517,587 B2
(45) Date of Patent: *Dec. 6, 2022

(54) DRUG THERAPY TO INHIBIT CHEMOTHERAPY-INDUCED ADVERSE EFFECTS AND RELATED PHARMACEUTICAL COMPOSITIONS, DIAGNOSTICS, SCREENING TECHNIQUES AND KITS

(71) Applicant: YALE UNIVERSITY, New Haven, CT (US)

(72) Inventors: Barbara Ehrlich, New Haven, CT (US); Sara Rockwell, Madison, CT (US); Jennifer Benbow, Fort Mill, SC (US)

(73) Assignee: YALE UNIVERSITY, New Haven, CT (US)

( * ) Notice: Subject to any disclaimer, the term of this patent is extended or adjusted under 35 U.S.C. 154(b) by 17 days.

This patent is subject to a terminal disclaimer.

(21) Appl. No.: 15/611,908

(22) Filed: Jun. 2, 2017

(65) Prior Publication Data
US 2017/0333474 A1  Nov. 23, 2017

Related U.S. Application Data

(63) Continuation of application No. 14/112,678, filed as application No. PCT/US2012/035381 on Apr. 27, 2012, now Pat. No. 9,700,579.

(60) Provisional application No. 61/479,431, filed on Apr. 27, 2011, provisional application No. 61/479,471, filed on Apr. 27, 2011.

(51) Int. Cl.
| | |
|---|---|
| A61K 31/337 | (2006.01) |
| A61K 33/14 | (2006.01) |
| A61K 38/57 | (2006.01) |
| A61K 45/06 | (2006.01) |
| A61K 31/20 | (2006.01) |
| A61K 31/416 | (2006.01) |
| A61K 31/19 | (2006.01) |
| A61K 31/437 | (2006.01) |
| A61K 31/5415 | (2006.01) |
| A61K 33/00 | (2006.01) |
| G01N 33/50 | (2006.01) |

(52) U.S. Cl.
CPC ............. *A61K 33/14* (2013.01); *A61K 31/19* (2013.01); *A61K 31/20* (2013.01); *A61K 31/337* (2013.01); *A61K 31/416* (2013.01); *A61K 31/437* (2013.01); *A61K 31/5415* (2013.01); *A61K 33/00* (2013.01); *A61K 38/57* (2013.01); *A61K 45/06* (2013.01); *G01N 33/5044* (2013.01)

(58) Field of Classification Search
None
See application file for complete search history.

(56) References Cited

U.S. PATENT DOCUMENTS

| | | |
|---|---|---|
| 9,700,579 B2 | 7/2017 | Ehrlich |
| 2010/0324082 A1 | 12/2010 | Johnson |

FOREIGN PATENT DOCUMENTS

| | | |
|---|---|---|
| WO | 2008115919 A2 | 9/2005 |
| WO | 2006063048 A2 | 6/2006 |
| WO | 2007087572 A2 | 8/2007 |
| WO | 2007146087 A2 | 12/2007 |

OTHER PUBLICATIONS

Crespo-Biel (Neuropharmacology 56 (2009) 422-428).*
Peters (BrainResearch 1168 (2007) 46-59).*
Peters 2 (Experimental Neurology 203 (2007) 42-54).*
Ji (The Journal of Neuroscience, Apr. 14, 2010 • 30(15):5451-5464).*
Hafner (Nursing2020, Aug. 2009, vol. 39 No. 8, p. 42-45).*
Arehart-Treichel (Psychiatry Online, Psychiatric News, Jul. 6, 2010; https://psychnews.psychiatryonline.org/doi/10.1176/pn.45.14.psychnews_45_14_023).*
De Sarno (J Immunol 2008; 181:338-345).*
Nahman (Innate Immunity, 18(3) 447-458, Oct. 12, 2011).*
Argyriou, "Either Called "Chemobrain" or "Chemofog," the Long-Term Chemotherapy-Induced Cognitive Decline in Cancer Survivors Is Real", Journal of Pain and Symptom Management, vol. 41, No. 1, pp. 126-139, Jan. 2011 (Year: 2011).*
Scripture, "Peripheral Neuropathy Induced by Paclitaxel: Recent Insights and Future Perspectives", Current Neuropharmacology, 4, pp. 165-172, 2006 (Year: 2006).*
Boehmerle W, et al. Chronic exposure to paclitaxel diminishes phosphoinositide signaling by calpain-mediated neuronal calcium sensor-1 degradation. PNAS, 2007;104(26):11103-11108.
Zhang K, et al. Paclitaxel accelerates spontaneous calcium oscillations in cardiomyocytes by interacting with NCS-1 and the InsP3R. Journal of Molecular and Cellular Cardiology, 2010;49:829-835.
Mo M, et al. Prevention of paclitaxel-Induced peripheral neuropathy by lithium pretreatment. The FASEB Journal, 2012;26:1-14.

(Continued)

Primary Examiner — Robert T. Crow
Assistant Examiner — John P Nguyen
(74) Attorney, Agent, or Firm — Henry D. Coleman; R. Neil Sudol

(57) ABSTRACT

The invention provides a method of treatment comprising reducing therapy-induced adverse effects (TIAE), including chemotherapy-induced adverse effects (CIAE), such as chemotherapy-induced peripheral neuropathy (CIPN) and/or chemotherapy-induced cardiovascular adverse effects (CI-CAE) in a subject being treated with a CIAE-inducing anti-cancer active ingredient by co-administering to the subject a pharmaceutically effective amount of a NCS-1-protective composition. Related pharmaceutical compositions, diagnostics and screening techniques are also provided.

18 Claims, 19 Drawing Sheets

(56) References Cited

OTHER PUBLICATIONS

Williams, et al. A common mechanism of action for three mood-stabilizing drugs. Nature, 2002;417:292-295.

Weng et al. Calpain inhibition protects against Taxol-induced sensory neuropathy. Brain, 2004;127:671-679.

Kurzrock R, et al. Safety, pharmacokinetics and activity of GRN1005, a novel conjugate of angiopep-2, a peptide facilitating brain penetration, and paclitaxel, in patients with advanced solid tumors. Mol Cancer Ther, 2011. Published online at doi:10.1158/1535-7163. MCT-11-0566.

Taraboletti G, et al. Antiangiogenic and Antitumor Activity of IDN 5390, a New Taxane Derivative. Clin Cancer Res, 2002;8:1182-1188.

Licht RW, et al. The effect of chronic lithium treatment on the calibre of axons and nerve fibres in the rat sural nerve. European Neuropsychopharmacology, 1997;7:95-98.

Johnston SR, et al. Peripheral neuropathy associated with lithium toxicity. J Neurol Neurosurg Psychiatry, 1991;54:1019-1020.

Can A, et al. Molecular actions and clinical pharmacogenetics of lithium therapy. Pharmacology, Biochemistry, and Behavior, 2014;123:3-16.

Oruch R, et al. Lithium: A review of pharmacology, clinical uses, and toxicity. European Journal of Pharmacology, 2014;740:464-473.

Keltner NL, et al. Irreversible Lithium-Induced Neuropathy: Two Cases. Perspectives in Psychiatric Care, 2008;44(4):290-293.

Blachford C, et al. Discrete proteolysis of neuronal calcium sensor-1 (NCS-1) by mu-calpain disrupts calcium binding. Cell Calcium, 2009;46:257-262.

Schlecker, et al. Neuronal calcium sensor-1 enhancement of InsP3 receptor activity is inhibited by therapeutic levels of lithium. The Journal of Clinical Investigation, 2006;116(6).

Siau, et al. Dysregulation of Cellular Calcium Homeostasis in Chemotherapy-Evoked Painful Peripheral Neuropathy. Anesth Analg, 2006;102(5):1485-1490.

Ledeboer A, et al. Novel approaches to control paclitaxel-induced neuropathic pain: Efficacy of interleukin-10 gene therapy and the blood-brain barrier permeable glial modulator, AV411. Brain, Behavior and Immunity, 2006;20(3):e43.

Petrini M, et al. Is lithium able to reverse neurological damage induced by vinca alkaloids? Short Communication. J Neural Transm, 1999;106:569-575.

Rahimi Balaei M, et al. The modulatory effect of lithium on doxorubicin-induced cardiotoxicity in rat. European Journal of Pharmacology, 2010;641(2-3):193-198.

Yang ES, et al. Lithium-mediated protection of hippocampal cells involves enhancement of DNA-PK-dependent repair in mice, Journal of Clinical Investigation, 2009;119(5):1124-1135.

Huang L, et al. 3-Nitropropionic Acid is a Suicide Inhibitor of Mitochondrial Respiration That, upon Oxidation by Complex II, Forms a Covalent Adduct with a Catalytic Base Arginine in the Active Site of the Enzyme. The Journal of Biological Chemistry, 2006;281(9):5965-5972.

Jakobsson E, et al. Towards a Unified Understanding of Lithium Action in Basic Biology and its Significance for Applied Biology. J Membrane Biol, 2017;250:587-604.

Lazzara CA, Kim YH. Potential application of lithium in Parkinson's and other neurodegenerative diseases. Frontiers in Neurosciences, 2015;9:Article 403.

Lueke K, et al. Basic presynaptic functions in hippocampal neurons are not affected by acute or chronic lithium treatment. J Neural Transm, 2014;121:211-219.

Machado-Vieira R, et al. The role of lithium in the treatment of bipolar disorder: convergent evidence for neurotrophic effects as a unifying hypothesis. Bipolar Disord, 2009;11:92-109.

Milutinovic A. Lithium chloride could aggravate brain injury caused by 3-nitropropionic acid. Bosn J Basic Med Sci, 2016;16(4):261-267.

Sasaki T, et al. Lithium-induced activation of Akt and CaM kinase II contributes to its neuroprotective action in a rat microsphere embolism model. Brain Research, 2006;1108:98-106.

Young W. Review of Lithium Effects on Brain and Blood. Cell Transplantation, 2009;18:951-975.

Levy NA, Janicak PG. Calcium channel antagonists for the treatment of bipolar disorder. Bipolar Disorders, 2000;2:108-119.

Boehmerle W, et al. Paclitaxel induces calcium oscillations via an inositol 1,4,5-triphosphate receptor and neuronal calcium sensor 1-dependent mechanism. PNAS, 2006;103(48):18356-18361.

Benbow JH, Degray B, Ehrlich BE. Protection of Neuronal Calcium Sensor 1 Protein in Cells Treated with Paclitaxel. The Journal of Biological Chemistry, 2011;286(40):34575-34582.

Benbow JH, et al. Inhibition of Paclitaxel-induced Decreased in Calcium Signaling. The Journal of Biological Chemistry, 2012;287(45):37907-37916.

Baudry M, Bi X. Calpain-1 and Calpain-2: The Yin and Yang of Synaptic Plasticity and Neurodegeneration. Trends in Neurosciences, 2016;39(4):235-245.

Buterbaugh GG, Michelson HB, Keyser DO. Status Epilepticus Facilitated by Pilocarpine in Amygdala-Kindled Rats. Experimental Neurology, 1986;94:91-102.

Jope RS, Morrisett RA, Snead OC. Characterization of Lithium Potentiation of Pilocarpine-Induced Status Epilepticus in Rats. Experimental Neurology, 1986;91:471-480.

Nagayoshi, et al. Hippocampal calpain is required for the consolidation and reconsolidation but not extinction of contextual fear memory. Molecular Brain, 2017;10:61.

Zadran S, et al. Brain-Derived Neurotrophic Factor and Epidermal Growth Factor Activate Neuronal m-Calpain via Mitogen-Activated Protein Kinase-Dependent Phosphorylation. The Journal of Neuroscience, 2010;30(3):1086-1095.

Hong SL, et al. Tranylcypromine and 15-Hydroperoxyarachidonate Affect Arachidonic Acid Release in Addition to Inhibition of Prostacyclin Synthesis in Calf Aortic Endothelial Cells. The Journal of Biological Chemistry, 1980;255(2):9538-9540.

Chang MCJ, Jones CR. Chronic Lithium Treatment Decreases Brain Phospholipase A2 Activity. Neurocemical Research, 1998;23(6):887-892.

Klein PS, Melthon DA. A molecular mechanism for the effect of lithium on development. Proc Natl Acad Sci USA, 1996;93:8455-8459.

Basselin M, et al. Chronic lithium administration attenuates up-regulated brain arachidonic acid metabolism in a rat model of neuroinflammation. Journal of Neurochemistry, 2007;102:761-772.

Mezni A, et al. Lithium induced oxidative damage and inflammation int he rat's heart: Protective effect of grape seed and skin extract. Biomedicine & Pharmacotherapy, 2017;95:1103-1111.

Koh PO, et al. Up-regulation of neuronal calcium sensor-1 (NCS-1) in the prefrontal cortex of schizophrenic and bipolar patients. PNAS, 2003;100(1):313-317.

Muller CJ, et al. Pilocarpine vs. lithium-pilocarpine for induction of status epilepticus in mice: Development of spontaneous seizures, behavioral alterations and neuronal damage. European Journal of Pharmacology, 2009;619:15-24.

Murphy DL, et al. Inhibition by lithium of prostaglandin E1 and norepinephrine effects on cyclic adenosine monophosphate production in human platelets. Clinical Pharmacology and Therapeutics, 1973;14(5):810-814.

Rinker JR, et al. A retrospective review of lithium usage in veterans with multiple sclerosis. Multiple Sclerosis and Related Disorder, 2013;2:327-333.

Mo M, et al. Prevention of paclitaxel-induced peripheral neuropathy by lithium pretreatment. FASEB J, 2012;26:1-14.

Chaung DM, et al. Neuroprotective effects of lithium in cultured cells and animal models of diseases. Bipolar Disorders, 2002;4:129-136.

Bell AJ, et al. Lithium neurotoxicity at normal therapeutic levels. The British Journal of Psychiatry, 1993;162:689-692.

Dethy S, et al. Cerebellar spongiform degeneration induced by acute lithium intoxication in the rat. Neuroscience Letters, 1997;224:25-28.

(56) References Cited

OTHER PUBLICATIONS

Kallen B, Tandberg A. Lithium and pregnancy, a cohort study on manic-depressive women. Acta psychiatr scand, 1983;68:134-139.
Kores B, Lader MH. Irreversibly Lithium Neurotoxicity: An Overview. Clinical Neuropharmacology, 1997;20(4):283-299.
Lang EJ, Davis SM. Lithium neurotoxicity: the development of irreversible neurological impairment despite standard monitoring of serum lithium levels. Journal of Clinical Neuroscience, 2002;9(3): 308-309.
Lei P, et al. Lithium suppression of tau induces brain iron accumulation and neurodegeneration. Molecular Psychiatry, 2017(22)396-406.
Nemeth ZH, et al. Lithium Induces NF-kB Activation and Interleukin-8 Production in Human Intestinal Epithelial Cells. The Journal of Biological Chemistry, 2002;277(10):7713-7719.
Newman PK, Saunders M. Lithium neurotoxicity. Postgraduate Medical Journal, 1979;55:701-703.
Rossi FH, et al. Permanent Cerebellar Degeneration After Acute Hyperthermia with Non-toxic Lithium Levels: a Case Report and Review of Literature Cerebellum, 2017;16:973-978.
Weinstein MR, Goldfield MD. Cardiovascular Malformations with Lithium Use During Pregnancy. Am J Psychiatry, 1975;132(5):529-531.
Nguyen LD, et al. Pharmacological rescue of cognitive function in a mouse model of chemobrain. Molecular Neurodegeneration, 2021;16(41):1-16.
Nguyen LD, et al. Comprehensive somatosensory and neurological phenotyping of NCS1 knockout mice. Scientific Reports, 2021;11:2372 https://doi.org/10.1038/s41598-021-81650-5.

\* cited by examiner

Non_Treated
800ng/mL Taxol
CAST_Taxol $N=18-20$, ***$=p<0.0008$, *$=p<0.0223$ ered by myelin degradation) associated with many approved anti-cancer treatments both extends and improves the quality of life of cancer patients, and results in significant near-term clinical benefits such as decreased tumor volume.
DRUG THERAPY TO INHIBIT CHEMOTHERAPY-INDUCED ADVERSE EFFECTS AND RELATED PHARMACEUTICAL COMPOSITIONS, DIAGNOSTICS, SCREENING TECHNIQUES AND KITS

RELATED APPLICATIONS

This application claims priority from and is a continuation application of U.S. national phase application Ser. No. 14/114,678 filed on Oct. 18, 2013, which is a U.S. national phase patent application of International Patent Application No. PCT/US2012/035381 filed Apr. 27, 2012 of same title, which claims priority from U.S. Provisional Application Ser. No. 61/479,431, filed Apr. 27, 2011, entitled "Drug therapy to prevent chemotherapy-induced polyneuropathy (Repositioning of Li Salt and other agents to treat bipolar disorders)" and U.S. Provisional Application Ser. No. 61/479,471, filed Apr. 27, 2011, entitled "Drug therapy to prevent chemotherapy-induced polyneuropathy (Repositioning of AV-411 (ibudilast)", the complete disclosures of which are hereby incorporated by reference in their entirety.

GOVERNMENT SUPPORT

This invention was made with government support under W81XWH-10-1-0033 awarded by the U.S. Department of Defense Army Medical Research and Material Command and under DK057751 awarded by National Institute of Health. The government has certain rights in the invention.

FIELD OF THE INVENTION

The present invention is directed to a method of treatment comprising reducing therapy-induced adverse effects (TIAE), including chemotherapy-induced adverse effects (CIAE) including calcium signaling disregulation generally, including especially, neuropathy/peripheral neuropathy (CIN/CIPN) and cardiovascular adverse effects such as cardiac arrhythmias/cardiac dysfunction (CICAE) and related symptoms, including central nervous system adverse effects, such as cognitive effects (especially reduced cognition) and adverse effects which are caused by myelin degradation in a subject being treated with a CIAE-inducing anti-cancer active ingredient by co-administering to the subject in need a pharmaceutically effective amount of a NCS-1-protective composition. Related pharmaceutical compositions, diagnostics, screening techniques and drug discovery and selection are also provided.

BACKGROUND OF THE INVENTION

Chemotherapy-induced adverse effects (CIAE) including peripheral neuropathy and cardiovascular adverse effects, among others, are painful and often irreversible side-effects of treatment that affects many cancer patients who undergo chemotherapy. CIAE interferes with a patient's daily living and impairs quality of life. More importantly, CIAE is a concern because these adverse effects can result in chemotherapy dose reductions and discontinuation of treatment. The cellular mechanisms responsible for CIAE are unknown and there is no standard treatment for the prevention or management of CIAE, including chemotherapy induced calcium signaling disregulation, neuropathy/peripheral neuropathy (CIN/CIPN) and chemotherapy induced cardiovascular adverse effects (CICAE), among other adverse effects.

For example, paclitaxel (Taxol®) is the most effective drug for treating breast and ovarian cancer. A major side-effect of treatment with paclitaxel is peripheral neuropathy. Approximately thirty percent of the women treated with paclitaxel are affected by irreversible CIPN and suffer discomfort and pain. To date, elucidating the cellular mechanisms through which paclitaxel and several other commonly used anti-cancer drugs including vincristine cause CIAE, including CIN/CIPN and/or CICAE has proven difficult and many paclitaxel (Taxol®) treated patients are at risk of discontinuing potentially life-extending treatments because of their inability to tolerate CIAE.

Patients treated with paclitaxel have been shown to develop arrhythmias and cardiac dysfunction (chemotherapy induced cardiovascular adverse effects or CICAE) that has been linked to dysregulated calcium signaling. See for example, Yeh, et al., Cardiovascular complications of cancer therapy: incidence, pathogenesis, diagnosis, and management. *Journal of the American College of Cardiology* 53, 2231-2247 (2009) and Zhang, et al., Paclitaxel accelerates spontaneous calcium oscillations in cardiomyocytes by interacting with NCS-1 and the InsP3R. *Journal of molecular and cellular cardiology* 49, 829-835 (2010). Cardiomyocytes isolated from mice treated with paclitaxel show an increase in the frequency of spontaneous calcium oscillations. These changes in cardiomyocytes result from the increased interaction of NCS-1 with the InsP3R[31].

Thus, strategies are needed to prevent unwanted CIAE-related related adverse effects of chemotherapy, including calcium signaling disregulation, CIN/CIPN and/or CICAE without altering the ability to treat the cancer. The need exists for methods of treatment that alleviate the peripheral neuropathy that is often suffered by patients who undergo treatment with one or more anti-cancer drugs such as paclitaxel (Taxol®).

SUMMARY OF THE INVENTION

Until now, no evidence existed for the use of approved drugs for the prevention of CIAE, including at least one or more of calcium signaling disregulation (CSD), CIN/CIPN and/or CICAE, among other effects (such as central nervous system effects of reduced cognition/cognitive impairment and adverse effects caused by myelin degradation). Due to our unique understanding of the off-target toxicity of certain classes of chemotherapy, we have discovered how to ameliorate and/or prevent CIAE, including calcium signaling disregulation, CIN/CIPN and/or CICAE and related symptoms, including central nervous system adverse effects, such as cognitive effects (especially including reduced cognition) and adverse effects which are caused by myelin degradation, through concomitant administration of certain neurologically-protective compositions and anti-cancer medications. The novel treatment regimens and pharmaceutical compositions described herein protect cells from unnecessary damage and maintain the anti-cancer efficacy of established chemotherapeutic drugs. Notably, ameliorating and/or preventing CIAE, including calcium signaling disregulation, CIN/CIPN and/or CICAE, among other effects (such as central nervous system effects of reduced cognition/cognitive impairment and adverse effects caused by myelin degradation) associated with many approved anti-cancer treatments both extends and improves the quality of life of cancer patients, and results in significant near-term clinical benefits such as decreased tumor volume.

In one aspect of our invention, we have found that neuronal calcium sensor 1 (NCS-1) is a novel binding protein for taxanes, vinca alkaloids and radiosensitizing agents, three classes of drugs that are commonly used to treat prevalent cancers. Two of these chemotherapeutic drug classes, the taxanes and vinca alkaloids halt cell division by targeting microtubule assembly. Remarkably, despite their distinct mechanisms of action, these drugs start the cascade to CIAE, including calcium signaling disregulation, CIPN and/or CICAE, among other effects (such as central nervous system effects of reduced cognition/cognitive impairment and adverse effects caused by myelin degradation) after binding to NCS-1 via a mechanism that is microtubule independent. Using the crystal structure of NCS-1, we have laid the foundation for structure-guided discovery of taxane and vinca alkaloid analogs that target microtubule assembly without binding to NCS-1 and minimize CIAE, including calcium signaling disregulation, CIN/CIPN and/or CICAE, among other effects (such as central nervous system effects of reduced cognition/cognitive impairment and adverse effects caused by myelin degradation).

More specifically, we have noted that with chemotherapeutic drugs there is an enhanced $Ca^{2+}$ signal which leads to hyper-activation of neurons and activation of enzymes that lead to pathological changes in the neurons (calcium signaling disregulation). Our previous studies showed the functional interactions among paclitaxel, NCS-1 and the inositol 1,4,5 trisphosphate receptor (InsP3R). Ehrlich, et al., Paclitaxel induces calcium oscillations via an inositol 1,4,5-trisphosphate receptor and neuronal calcium sensor 1-dependent mechanism, *Proc Natl Acad Sci USA*. 2006 Nov. 28; 103(48): 18356-18361. We also found that addition of paclitaxel activated calpain, which led to the degradation of NCS-1. In preliminary studies, we were able to prevent NCS-1 degradation by inhibiting calpain. With this background, we elucidated molecular mechanisms implicated in NCS-1 degradation and thereby identified optimal pathways to protect NCS-1 levels in cells. Hence, the methods and compositions described herein interfere with these pathological cascades and avoid the peripheral neuropathy associated with chemotherapeutic treatments.

In a second aspect of our invention, we have identified pharmaceutical agents ("protector drugs" or "NCS-1-protective compositions"), including lithium and AV411 (ibudilast), among others, as described herein, that block the pathological cascade that causes CIAE, including calcium signaling disregulation, including especially, neuropathy/peripheral neuropathy (CIN/CIPN) and cardiovascular adverse effects such as cardiac arrhythmias/cardiac dysfunction (CICAE) and related symptoms, including central nervous system adverse effects, such as cognitive effects (especially reduced cognition) and adverse effects which are caused by myelin degradation which are associated with cancer therapy using taxanes, vinca alkaloids and radiation sensitizing agents. An NCS-1 protective composition is any compound or composition that ameliorates or inhibits CIAE, as otherwise described herein. Tests in cells and in mice treated with a taxane at levels that reliably induce CIAE show that the protector drugs inhibit and/or prevent CIAE, including CIPN and/or CICAE, among other effects (such as central nervous system adverse effects of reduced cognition/cognitive impairment and adverse effects caused by myelin degradation) when administered contemporaneously (i.e, at about the same time, before, including substantially before or even after) with dosing with a taxane, vinca alkaloid or radiation sensitizing agent as otherwise described herein. The protective NCS-1-protective compositions as described herein bind to NCS-1 and avoid the progression of the undesirable CIAE pathological cascade. They also are well-tolerated, have in most cases received marketing approval, and are highly amenable to combination formulation or administration consistent with the existing standard of care. Further, they do not interfere with the microtubule effects of the taxanes and vinca alkaloids (FIGS. 2 and 2A).

Therefore, in accordance with our invention, CIAE, including calcium signaling disregulation, CIN/CIPN and/or CICAE and related symptoms, including central nervous system adverse effects, such as cognitive effects (especially reduced cognition) and adverse effects which are caused by myelin degradation, is ameliorated and/or prevented by administration of preselected analogs of chemotherapeutic drugs (including pharmaceutically acceptable salts) or by timely administration or co-administration of one or more NCS-1-protective compositions (including pharmaceutically acceptable salts) as described herein.

In a third aspect of our invention, we have found that the non-microtubule protein target of the protector drugs (NCS-1-protective compositions as described herein) varies significantly (e.g. nearly eight-fold when measured in tissue taken from human breast cancer samples). This finding can be used to indicate a patient's susceptibility to the chemotherapy adverse effects such as CIN/CIPN and/or CICAE and related symptoms, including central nervous system adverse effects, such as cognitive effects (especially reduced cognition) and adverse effects which are caused by myelin degradation. An adverse effect prognosis or a favorable prognosis to chemotherapy with a taxane, a vinca alkaloid or a radiation sensitizing agent as otherwise described herein can be determined in vitro, in vivo or in silica by determining NCS-1 expression levels in a cancer cell sample obtained from a subject who is a candidate for treatment with an active ingredient which might induce CIAE, including CIPN and/or CICAE, among other adverse effects as described herein.

Thus, in one embodiment, the invention provides a method of treatment comprising preventing or reducing chemotherapy-induced adverse effects (CIAE) including chemically calcium signaling disregulation, induced neuropathy/peripheral neuropathy (CIN/CIPN) and/or chemically induced cardiovascular adverse effects CICAE and related symptoms, including central nervous system adverse effects, such as cognitive effects (especially reduced cognition) and adverse effects which are caused by myelin degradation in a subject being treated with a CIAE inducing anti-cancer active ingredient by co-administering to the subject a pharmaceutically effective amount of a NCS-1-protective composition as described herein.

In certain embodiments, more than one type of NCS-1-protective composition is co-administered (including administration much earlier than administration of the CIAE-inducing anticancer active ingredient) to the subject and the dosages of the co-administered NCS-1-protective compositions are the same or different. In still other embodiments, more than one type of CIAE-inducing anti-cancer active ingredient and NCS-1-protective composition are co-administered.

In certain embodiments, the CIAE-inducing anti-cancer active ingredient is selected from the group consisting of a taxane a vinca alkaloid, a radiation sensitizing agent (including pharmaceutically acceptable salts of these compounds or agents) or mixtures thereof, and the NCS-1-protective composition is a calpain inhibitor (including a pharmaceutically acceptable salt). A natural calpain inhibitor is calpastatin. Non-limiting examples of other calpain inhibitors that can be used include AK275, calpain inhibitor I, calpain inhibitor II, calpain inhibitor III, calpain inhibitor IV, calpain inhibitor V, calpain inhibitor XI, and calpain inhibitor XII.

In other embodiments, the CIAE-inducing anti-cancer active ingredient is selected from the group consisting of a taxane (e.g. paclitaxel/Taxol® or docetaxel/Taxoterel®), a vinca alkaloid (e.g. vinblastine, vincristine, vindesine, and vinorelbine, preferably vincristine), a radiosensitizing agent (e.g. nimorazole, metronidazole or misonidazole) and mixtures thereof, and the NCS-1-protective composition is selected from the group consisting of AV411, lithium (e.g. lithium carbonate, lithium chloride or any pharmaceutically acceptable form of lithium), valproic acid, chlorpromazine, a calpain inhibitor such as calpastatin and mixtures thereof.

In a preferred embodiment, the CIAE-inducing anti-cancer active ingredient is selected from the group consisting of paclitaxel (Taxol®), docetaxel (Taxoterel®, vincristine, metronidazole and mixtures thereof and the NCS-1-protective composition is selected from the group consisting of a calpain inhibitor, valproic acid, chlorpromazine and mixtures thereof.

In still another embodiment, the CIAE-inducing anti-cancer active ingredient is selected from the group consisting of paclitaxel (Taxol®), docetaxel (Taxoterel®), vincristine, metronidazole and mixtures thereof and the NCS-1-protective composition is selected from the group consisting of AV411 (ibudilast), a AV411 analog (e.g. AV1013, or as otherwise described in PCT patent application WO2007146087, which is incorporated by reference herein) lithium, valproic acid, chlorpromazine and a calpain inhibitor, such as calpastatin, AK275, calpain inhibitor I, calpain inhibitor II, calpain inhibitor III, calpain inhibitor IV, calpain inhibitor V, calpain inhibitor XI, calpain inhibitor XII and mixtures thereof.

In another preferred embodiment, the CIAE-inducing anti-cancer active ingredient is selected from the group consisting of paclitaxel (Taxol®), docetaxel (Taxoterel®), vincristine and mixtures thereof and the NCS-1-protective composition is selected from the group consisting of AV411 (ibudilast), lithium, valproic acid, a calpain inhibitor (e.g. calpastatin, AK275, calpain inhibitor I, calpain inhibitor II, calpain inhibitor III, calpain inhibitor IV, calpain inhibitor V, calpain inhibitor XI, calpain inhibitor XII and mixtures thereof) and chlorpromazine.

In another embodiment, the invention provides a method of improving the tolerance of a subject undergoing anti-cancer treatment with a CIAE-inducing anti-cancer active ingredient, the method comprising co-administering to the subject a NCS-1-protective composition in an effective amount.

In still another embodiment, the invention provides a method of treatment comprising enhancing the likelihood of a favorable prognosis in a subject undergoing anti-cancer treatment with a CIAE-inducing anti-cancer active ingredient by co-administering to the subject a NCS-1-protective composition in an effective amount.

In still another embodiment, the invention provides a method of inhibiting and/or reducing the likelihood of peripheral neuropathy in a subject undergoing anti-cancer treatment with a CIAE-inducing anti-cancer active ingredient by co-administering to the subject a NCS-1-protective composition in an effective amount.

In still another embodiment, the invention provides a method of treatment comprising reducing the volume of a tumor expressed by a subject undergoing anti-cancer treatment with CIAE-inducing anti-cancer active ingredient by co-administering to the subject a NCS-1-protective composition in an effective amount.

In a preferred embodiment, the invention provides a method of treatment comprising reducing or inhibiting chemotherapy-induced adverse effects CIAE) including one or more of calcium signaling disregulation, chemically induced neuropathy/peripheral neuropathy (CIPN) and/or chemically induced cardiovascular adverse effects (CICAE) and related symptoms, including central nervous system adverse effects, such as cognitive effects (especially reduced cognition) and adverse effects which are caused by myelin degradation in a subject who suffers from breast cancer, ovarian, lung cancer and/or prostate cancer and who is being treated with Paclitacel (Taxol®), docetaxel (Taxoterel®) or a vinca alkaloid such as vincristine, etc., by co-administering to the subject a pharmaceutically effective amount of a NCS-1-protective composition selected from the group consisting of AV411 (ibudilast), an AV411 analog (e.g., AV 1013, among others), lithium, valproic acid, a calpain inhibitor (as otherwise described herein), chlorpromazine and mixtures thereof.

In another preferred embodiment, the invention provides a method of treating a subject who suffers from a cancer associated with tumor expression and for whom administration of a CIAE-inducing anti-cancer active ingredient is indicated, the method comprising reducing tumor volume in the subject to an extent which is greater than tumor volume reduction achieved by CIAE-inducing anti-cancer active ingredient therapy (including one agent or combination of agents) by co-administering a NCS-1-protective composition to the subject between about one to about four hours prior to administration of the CIAE-inducing anti-cancer active ingredient "Reducing tumor volume in the subject to an extent which are greater than tumor volume reduction achieved by CIAE-inducing anti-cancer active ingredient monotherapy" includes reducing tumor volume through co-administration of the NCS-1-protective composition by at least about 20%, or 19%, or 18%, or 17%, or 16%, or 15%, or 14%, or 13%, or 12%, or 11%, or 10%, or 9%, or 8%, or 7%, or 6%, or 5%, or 4%, or 3%, or 2%, or 1%, or 0.5%, or 0.1%, or 0.05%, or 0.01% when compared to tumor volumes observed in CIAE-inducing anti-cancer active ingredient monotherapy over a comparable treatment period.

In certain embodiments, the NCS-1-protective composition is co-administered to the subject prior to, contemporaneously with, or after administration of the CIAE-inducing anti-cancer active ingredient, Preferably, the NCS-1-protective composition is administered to the subject prior to the administration of the CIAE-inducing anti-cancer active ingredient (e.g. around four or more, or around three, or around two, or around one hour or less as otherwise described herein before administration of the CIAE-inducing anti-cancer active ingredient(s)).

In yet another embodiment, the present invention is directed to a method of screening for candidate compounds useful in treatment in combination with a NCS-1 protective agent the method comprising (a) determining values for either the binding affinity of a candidate compound for NCS-1 or the extent to which the candidate compound up-regulates NCS-1 activation of InsP3R dependent $Ca^{2+}$ release; and (b) comparing binding affinity values or InsP3R dependent $Ca^{2+}$ release values of said candidate compound to control values based on (1) the binding affinity of a taxane, a vinca alkaloid or a radiation sensitizing agent and/or (2) InsP3R dependent $Ca^{2+}$ release values of a taxane, vinca alkaloid or a radiation sensitizing agent ascertained in second sample, wherein the candidate compound is identified as a potentially useful therapeutic compound for coadministration with a NCS-1 protective agent if its determined binding affinity is about the same as or more than the comparable control value or if its InsP3R dependent $Ca^{2+}$ release value is approximately equal to or more than the comparable control value.

In still another embodiment, the invention provides a method of determining the likelihood that a subject who suffers from a cancer and who is a candidate for treatment with an anti-cancer active ingredient will express CIAE, including calcium signaling disregulation, CIN/CIPN and/or CICAE and related symptoms, including central nervous system adverse effects, such as cognitive effects (especially reduced cognition) and adverse effects which are caused by myelin degradation as the result of such treatment, the method comprising determining NCS-1 levels in patient cancer cells prior to administration of the anti-cancer active ingredient, contacting the patient cancer cells with the anti-cancer active ingredient and thereafter measuring patient cancer cell NCS-1 levels, wherein a decrease in NCS-1 levels in patient cancer cells indicates an increased likelihood that the subject will express CIAE, including calcium signaling disregulation, CIN/CIPN and/or CICAE and related symptoms, including central nervous system adverse effects, such as cognitive effects (especially reduced cognition) and adverse effects which are caused by myelin degradation upon treatment with the anti-cancer active ingredient. This method can be conducted in vitro, in vivo, or in silica.

In still another embodiment, the invention provides a method of determining the likelihood that a patient who suffers from a cancer and who is a candidate for treatment with an anti-cancer active ingredient will express CIAE, including calcium signaling disregulation, CIN/CIPN and/or CICAE and related symptoms, including central nervous system adverse effects, such as cognitive effects (especially reduced cognition) and adverse effects which are caused by myelin degradation as the result of such treatment, the method comprising determining NCS-1 levels in patient cancer cells prior to administration of the anti-cancer active ingredient, comparing the determined NCS-1 levels to control NCS levels associated with benign InsP3R dependent $Ca^{2+}$ release values, wherein determined NCS-1 levels in excess of control NCS levels are indicative of an increased likelihood that the subject will express CIAE, including CIPN and/or CICAE and related symptoms, including central nervous system adverse effects, such as cognitive effects (especially reduced cognition) and adverse effects which are caused by myelin degradation upon treatment with the anti-cancer active ingredient. This method can be conducted in vitro, in vivo, or in silica.

In still a further embodiment, the invention provides a method of determining whether or not a subject who suffers from cancer is a candidate for chemotherapy with a taxane, a vinca alkaloid or a radiation sensitizing anticancer agent such that the patient will likely favorably respond to such anticancer therapy, the method comprising determining NCS-1 levels and/or InsP3R dependent $Ca^{2+}$ release values before therapy in a sample(s) (especially including a sample of cancer cells from cancer tissue) obtained from a patient prior to anticancer therapy, comparing the NCS-1 levels or InsP3R dependent $Ca^{2+}$ release values in said sample(s) obtained from said patient with control NCS-1 and/or InsP3R dependent $Ca^{2+}$ release values levels in sample(s) obtained from patients who have been successfully treated with taxane, vinca alkaloid and/or radiation sensitizer anticancer agents and determining that the patient is a candidate for anticancer therapy with taxane, vinca alkaloid and/or radiation sensitizing anticancer agents if the NCS-1 and/or InsP3R dependent $Ca^{2+}$ release values levels in said patient compare favorably (i.e., generally about the same as or higher) or unfavorably (generally, substantially lower) than the control NCS-1 and/or InsP3R dependent $Ca^{2+}$ release value levels.

In still another embodiment, the invention provides pharmaceutical composition comprising:
  (a) a pharmaceutically-effective amount of one or more anti-cancer active ingredients selected from the group consisting of a taxane, a vinca alkaloid, a radiosensitizing agent or a mixture thereof;
  (b) one or more NCS-1-protective compositions selected from the group consisting of AV411 (ibudilast), an AV411 (ibudilast) analog (e.g., AV1013), lithium, valproic acid, chlorpromazine and a calpain inhibitor; and optionally
  (c) a pharmaceutically-acceptable carrier, additive or excipient.

In still another embodiment, the invention provides a method of screening for compositions useful in the treatment of a cancer with a reduced likelihood of causing chemotherapy induced adverse effects, including peripheral neuropathy and/or cardiovascular adverse effects, the method comprising:
  (a) contacting or exposing a first sample of a cancer cell population with a candidate composition;
  (b) determining values for either the binding affinity of the candidate composition for NCS-1 or the extent to which the candidate composition up-regulates NCS-1 activation of InsP3R dependent $Ca^{2+}$ release; and
  (c) comparing binding affinity values or InsP3R dependent $Ca^{2+}$ release values to control values based on (1) the binding affinity of a taxane such as paclitaxel (Taxol®), docetaxel (Taxoterel®), a vinca alkaloid (preferably, vincristine) and/or a radiation sensitizing agent in a second sample of the cancer cell population and/or (2) InsP3R dependent $Ca^{2+}$ release values ascertained in an untreated second sample of the cancer cell population, wherein the candidate composition is identified as a potentially useful anti-cancer composition if its determined binding affinity is less than the comparable control value or if its InsP3R dependent $Ca^{2+}$ release value is approximately equal to or less than the comparable control value.

In preferred embodiments, a determined binding affinity or InsP3R dependent $Ca^{2+}$ release value is considered to be approximately equal to or less than a control value if the determined and control values vary by no more than about 20%, or 19%, or 18%, or 17%, or 16%, or 15%, or 14%, or 13%, or 12%, or 11%, or 10%, or 9%, or 8%, or 7%, or 6%, or 5%, or 4%, or 3%, or 2%, or 1%, or 0.5%, or 0.1%, or 0.05%, or 0.01%.

As explained further hereinafter, we have identified a novel binding protein for taxanes, vinca alkaloids and radiation sensitizing agents and also found several drugs individually appropriate for a novel therapy that may prevent CIAE, calcium signaling disregulation, including CIN/CIPN and/or CICAE and related symptoms, including central nervous system adverse effects, such as cognitive effects (especially reduced cognition) and adverse effects which are caused by myelin degradation. The novel binding protein, NCS-1, represents a newly identified molecular cascade that explains taxane- and vinca alkaloid-induced peripheral neuropathy. An analog of these chemotherapeutic drugs that does not bind to NCS-1 or exhibits reduced binding to NCS-1 will avoid or reduce the development of CIAE, including calcium signaling disregulation. CIN/CIPN and/or CICAE and related symptoms, including central nervous system adverse effects, such as cognitive effects (especially reduced cognition) and adverse effects which are caused by myelin degradation in chemotherapy patients. The protector drugs interfere with NCS-1 dependent pathological cascades and ultimately result in the prevention of CIAE, calcium signaling disregulation, including CIN/CIPN and/or CICAE and related symptoms, including central nervous system adverse effects, such as cognitive effects (especially reduced cognition) and adverse effects which are caused by myelin degradation in vivo. The protective agents we have identified have low toxicity and have been approved for decades for chronic administration. These analogs and protective drugs would be the first pharmacologic approaches that offer the ability to prevent CIAE, including calcium signaling disregulation, CIN/CIPN and/or CICAE and related symptoms, including central nervous system adverse effects, such as cognitive effects (especially reduced cognition) and adverse effects which are caused by myelin degradation while maintaining effective cancer therapy intervention with taxanes, vinca alkaloids and/or radiation sensitizing agents.

These and other aspects of the invention are described further in the Detailed Description of the Invention.

DETAILED DESCRIPTION OF THE INVENTION

Figure 1:
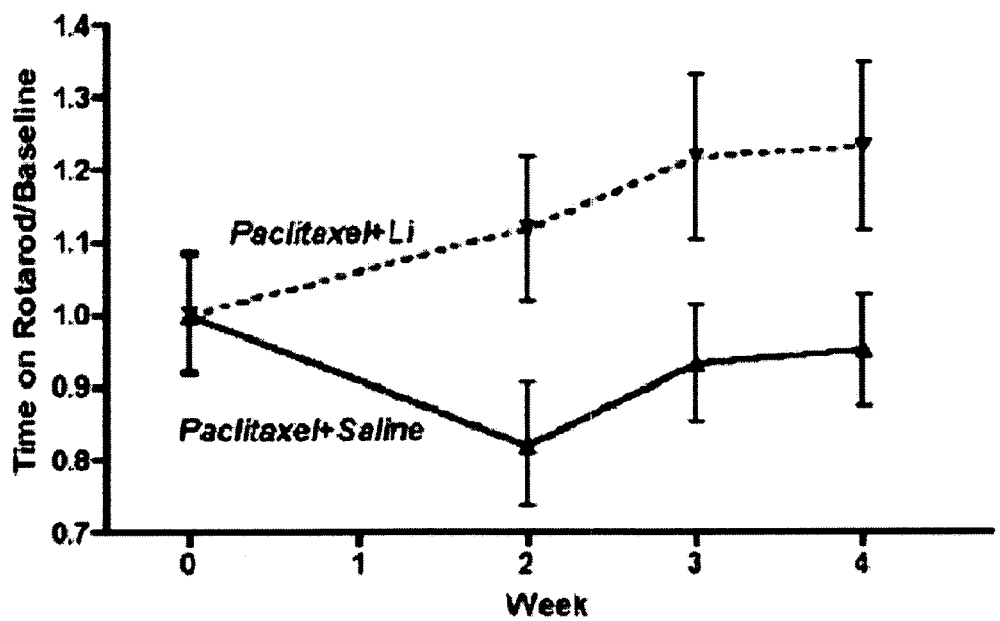
FIG. 1: Lithium protects mice from developing neuropathy; 10 mice/group; paclitaxel 4.5 mg/kg per ip injection, 4 injections Lithium 12.8 mg/kg ip injection 1 hour prior to paclitaxel
Figure 1:
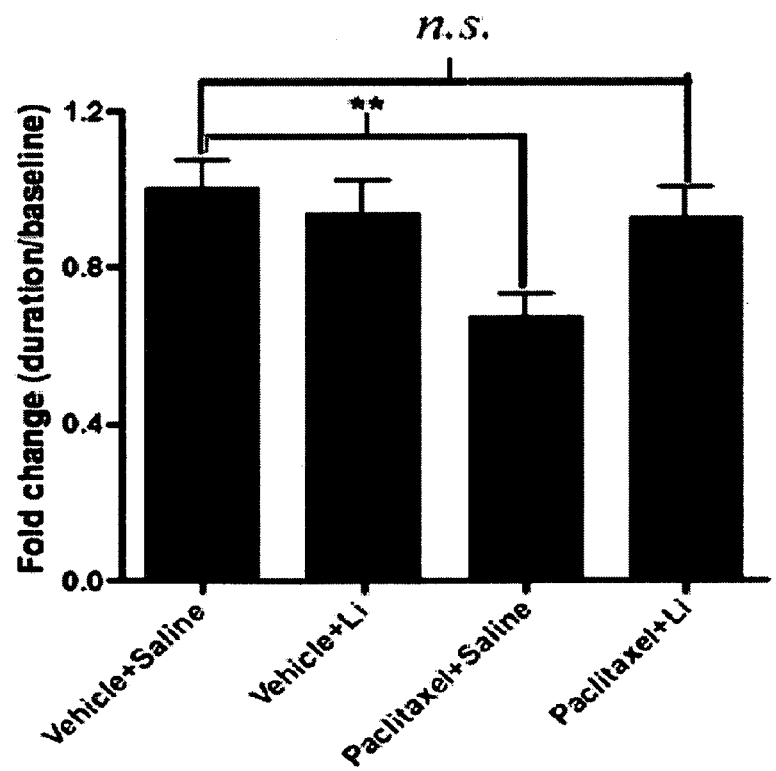

The following terms, among others, are used to describe the present invention. It is to be understood that a term which is not specifically defined is to be given a meaning consistent with the use of that term within the context of the present invention as understood by those of ordinary skill.

The term "compound" or "agent", as used herein, unless otherwise indicated, refers to any specific chemical compound disclosed herein and includes tautomers, regioisomers, geometric isomers as applicable, and also where applicable, optical isomers (e.g. enantiomers) thereof, as well as pharmaceutically acceptable salts (such that lithium or another agent refers to that agent where applicable and any pharmaceutically acceptable salt) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "patient" or "subject" is used throughout the specification within context to describe an animal, generally a mammal and preferably a human, to whom treatment, including prophylactic treatment (prophylaxis), with the methods and compositions according to the present invention is provided. For treatment of those conditions or disease states which are specific for a specific animal such as a human patient, the term patient refers to that specific animal, The terms "effective" or "pharmaceutically effective" are used herein, unless otherwise indicated, to describe an amount of a compound or composition which, in context, is used to produce or affect an intended result, whether that result relates to the inhibition of the effects of CIAE, including calcium signaling disregulation, CIN/CIPN and/or CICAE, or to potentiate the effects of a concomitant treatment of cancer as described herein or to be used in diagnosis, etc. as disclosed herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for or afflicted by a cancer and who suffers from or is at risk of developing CIAE, including calcium signaling disregulation, CIN/CIPN and/or CICAE, including lessening or suppression of at least one symptom of CIAE, including calcium signaling disregulation, CIN/CIPN and/or CICAE and/or cancer, delay in progression of a CIAE including calcium signaling disregulation, CIN/CIPN and/or CICAE-related symptom or a cancer-related symptom, or the reduction in likelihood of the onset of CIAE, including calcium signaling disregulation, CIN/CIPN and/or CICAE. Treatment, as used herein, encompasses both prophylactic and therapeutic treatment.

The term "therapy induced side effects" including "chemotherapy induced adverse effects" or "CIAE" refers to adverse side effects which occur secondary to the administration of certain types of therapeutic agents, especially including chemotherapy (which term includes radiation therapy with a radiation sensitizing agent), in particular, the taxanes, the vinca alkaloids and radiation sensitizing agents as otherwise described herein pursuant to the treatment of cancer in a patient. The terms chemotherapy and cancer therapy may be used synonymously within context herein and the term therapy subsumes chemotherapy and cancer therapy. The term CIAE includes calcium signaling disregulation, chemotherapy-induced neuropathy, including peripheral neuropathy (CIN/CIPN) and chemotherapy-induced cardiovascular adverse events (CICAE), which effects include cardiac arrythmias and cardiovascular dysfunction, including increased and/or decreased cardiovascular calcium signaling and increased spontaneous calcium oscillations.

Symptoms of chemotherapy induced neuropathy (CIN) or peripheral neuropathy (CIPN) include, but are not limited to, burning, tingling ("pins and needles" feeling), loss of feeling (can be numbness or just less ability to sense pressure, touch, heat, or cold), trouble using fingers to pick up or hold things, dropping things, balance problems, trouble with tripping or stumbling while walking, pressure or temperature hurt more than usual (mostly cold; this is called cold sensitivity), shrinking muscles, muscle weakness, trouble swallowing, constipation, trouble passing urine, blood pressure changes and altered nerve conduction velocity with decreased or no reflexes. A number of these symptoms are also associated with calcium signaling disregulation as well.

Symptoms of chemotherapy induced cardiovascular adverse events or CICAE include cardiac arrhythmia and cardiovascular dysfunction, especially including cardiovascular calcium signaling disregulation (increased or decreased calcium signaling) and/or increased spontaneous calcium oscillations. The term cardiac arrhythmia (also, cardiac dysrhythmia and irregular heartbeat) refers to any of a large and heterogeneous group of conditions in which there is abnormal electrical activity in the heart. The heartbeat may be too fast or too slow, and may be regular or irregular. Some arrhythmias are life-threatening, especially those which are chemotherapy-induced and they can result in cardiac arrest. Still others may not be associated with significant symptoms at all, but may predispose the patient to potentially life threatening stroke or embolism.

"Taxanes" include, but are not limited to, paclitaxel (Taxol®), docetaxel (Taxoterel®), taxane derivatives such as IDN 5390, GRN1005, the taxane derivatives described in EP 2330100A1, and the taxane derivatives described or referenced in *Bioscience, Biotechnology, and Biochemistry*, Vol. 76 (2012), No. 2 pp. 349-352.

"Radiation sensitizing compounds" include, but are not limited to nimorazole, metronidazole and misonidazole. In the present application these compounds are defined as chemotherapy agents and anticancer agents.

"Vinca alkaloids" include, but are not limited to, vinblastine, vincristine, vindesine and vinorelbine and the vinca alkaloids described or referenced in Holland-Frei *Cancer Medicine*. 6th edition, Kufe D W, Pollock R E, Weichselbaum R R, et al., editors. Hamilton (ON): BC Decker; 2003.

The taxanes, vinca alkaloids and/or radiation sensitizers, among other agents, belong to a group of compounds or agents referred to as CIAE-inducing anti-cancer active ingredients that during therapy, cause the modification, including post-translational modification, of NCS-1 or NCS-1 activity. Other agents, which may or may not be anticancer agents but which cause the same effect during therapy (for whatever purpose) are referred to herein as "therapy inducing adverse effect therapeutic agents" (TIAE-inducing therapeutic agents). This modification (of NCS-1 or NCS-1 activity) results in the development in the patient of CIAE (TIAE), including calcium signaling disregulation generally, including especially, neuropathy/peripheral neuropathy (CIN/CIPN) and cardiovascular adverse effects such as cardiac arrhythmias/cardiac dysfunction (CICAE) and related symptoms, including central nervous system adverse effects, such as cognitive effects (especially reduced cognition) and adverse effects which are caused by myelin degradation.

"NCS-1-related protein" includes, but is not limited to, NCS-1, FRQ1, ncs-1, ncs-2, ncs-3, Frequenin 1, Frequenin 2, neurocalein, hippocalcin, KChIP, NCS-1 Human Recombinant and homologs thereof.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated.

As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention. In certain preferred aspects, the cancer which is treated is lung cancer, breast cancer, ovarian cancer and/or prostate cancer.

The term "tumor" is used to describe a malignant or benign growth or tumefacent.

The term "additional anti-cancer compound", "additional anti-cancer drug" or "additional anti-cancer agent" is used to describe any compound (including its derivatives) which may be used to treat cancer. The "additional anti-cancer compound", "additional anti-cancer drug" or "additional anti-cancer agent" can be an anticancer agent which is distinguishable from a CIAE-inducing anticancer ingredient such as a taxane, vinca alkaloid and/or radiation sensitizing agent otherwise used as chemotherapy/cancer therapy agents herein. In many instances, the co-administration of another anti-cancer compound according to the present invention results in a synergistic anti-cancer effect. Exemplary anti-cancer compounds for co-administration with formulations according to the present invention include anti-metabolites agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and tyrosine kinase inhibitors or ABL kinase inhibitors (e.g. imatinib).

Anti-cancer compounds for co-administration include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvelcin; oxaliplatin; paclitaxel; pamidronate; pegademase; Pegaspargase; Pegfilgrastim; pentostatin; pipobroman; plicamycin; mithramycin; porfirner sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; vairubicin; valtorcitabine (monoval LDC); vinblastine; vinorelbine; zoledronate; and mixtures thereof, among others.

The term "co-administration" or "combination therapy" is used to describe a therapy in which at least two active compounds in effective amounts are used to treat cancer and/or CIAE, including calcium signaling disregution, CIN/CIPN and/or CICAE or another disease state or condition as otherwise described herein, either at the same time or within dosing or administration schedules defined further herein or ascertainable by those of ordinary skill in the art. Although the term co-administration preferably includes the administration of two active compounds to the patient at the same time, it is not necessary that the compounds be administered to the patient at the same time, although effective amounts of the individual compounds will be present in the patient at the same time. In addition, in certain embodiments, co-administration will refer to the fact that two compounds are administered at significantly different times, but the effects of the two compounds are present at the same time. Thus, the term co-administration includes an administration in which one active agent (especially an NCS-1 protective composition) are administered at approximately the same time (contemporaneously), or from about one to several minutes to about eight hours, about 30 minutes to about 6 hours, about an hour to about 4 hours, or even much earlier than the CIAE-inducing anti-cancer active ingredient as otherwise described herein including up to a day or substantially more. It is noted that in certain embodiments, the NCS-1 protective composition may be administered after the CIAE-inducing anti-cancer active ingredient and still have an ameliorative or protective effect.

Co-administered anticancer compounds can include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogarnicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate;

methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; vairubicin; valtorcitabine (monoval LDC); vinblastine; vinorelbine; zoledronate; and mixtures thereof, among others.

Co-administration of one of the formulations of the invention with another anticancer agent will often result in a synergistic enhancement of the anticancer activity of the other anticancer agent, an unexpected result. One or more of the present formulations may also be co-administered with another bioactive agent (e.g., antiviral agent, antihyperproliferative disease agent, agents which treat chronic inflammatory disease, among others as otherwise described herein).

"Tyrosine kinase inhibitors" include, but are not limited to imatinib, axitinib, bosutinib, cediranib, dasatinib, erlotinib, gefitinib, lapatinib, lestaurtinib, nilotinib, semaxanib, sunitinib, toceranib, vandetanib, vatalanib, sorafenib (Nexavar®), lapatinib, motesanib, vandetanib (Zactima®), MP-412, lestaurtinib, XL647, XL999, tandutinib, PKC412, AEE788, OSI-930, OSI-817, sunitinib maleate (Sutent®)) and N-(4-(4-aminothieno[2,3-d]pyrimidin-5-yl)phenyl)-N'-(2-fluoro-5-(trifluoromethyl)phenyl)urea, the preparation of which is described in United States Patent Application Document No. 2007/0155758.

Pharmaceutical compositions comprising combinations of an effective amount of at least one anti-cancer active ingredient (e.g., a taxane, vinca alkaloid and/or radiation sensitizing agent) and at least one NCS-1-protective composition according to the present invention, and/or one or more of the other additional anti-cancer compounds otherwise described herein, all in effective amounts, in combination with a pharmaceutically effective amount of a carrier, additive or excipient, represents a further aspect of the present invention.

The compositions used in methods of treatment of the present invention, and pharmaceutical compositions of the invention, may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions used in methods of treatment of the present invention, and pharmaceutical compositions of the invention, may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions used in methods of treatment of the present invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and the type of cancer treated, and the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of at least one anti-cancer active ingredient and at least one NCS-1-protective composition, optionally in combination with at least one additional anti-cancer active ingredient and/or NCS-1-protective composition.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

In certain non-limiting embodiments, an increase or a decrease in a subject or test sample of the level of measured NCS-1 levels or InsP3R dependent $Ca^{2+}$ release values as compared to a comparable levels of measured NCS-1 levels or InsP3R dependent $Ca^{1+}$ release values in a control subject or sample (which may include healthy subject(s), subject(s) with cancer or subject(s) who has/have successfully been treated with a taxane, vinca alkaloid and/or radiation sensitizing anticancer agent) can be an increase or decrease in the magnitude of approximately ±5,000-10,000%, or approximately ±2,500-5,000%, or approximately ±1,000-2,500%, or approximately ±500-1,000%, or approximately ±250-500%, or approximately ±100-250%, or approximately ±50-100%, or approximately ±25-50%, or approximately ±10-25%, or approximately ±10-20%, or approximately ±10-15%, or approximately ±5-10%, or approximately ±1-5%, or approximately ±0.5-1%, or approximately ±0.1-0.5%, or approximately ±0.01-0.1%, or approximately ±0.001-0.01%, or approximately ±0.0001-0.001%.

The values obtained from controls are reference values representing a known health status and the values obtained from test samples or subjects are reference values representing a known disease status. The term "control", as used herein, can mean a sample of preferably the same source (e.g. cancer cells, blood, serum, tissue etc.) which is obtained from at least one healthy subject or subject suffering from cancer, in order to be compared to the sample to be analyzed. In order to receive comparable results the control as well as the sample should be obtained, handled and treated in the same way. In certain examples, the number of individuals used to obtain a control value may be at least one, preferably at least two, more preferably at least five, most preferably at least ten, in particular at least twenty. However, the values may also be obtained from at least one hundred, one thousand or ten thousand individuals.

A level and/or an activity and/or expression of a translation product of a gene and/or of a fragment, or derivative, or variant of said translation product, and/or the level or activity of said translation product, and/or of a fragment, or derivative, or variant thereof, can be detected using an immunoassay, an activity assay, and/or a binding assay. These assays can measure the amount of binding between said protein molecule and an anti-protein antibody by the use of enzymatic (e.g. an antibody is linked to an enzyme which activates a fluorescent chromagen to provide a fluorescent dye for detection), chromodynamic, radioactive, magnetic, or luminescent (fluorophore or fluorescent moiety) labels (these molecules are generally referred to as reporters or reporter molecules) which are attached to either the anti-protein antibody or a secondary antibody which binds the anti-protein antibody. These are all standard and well-known in the art. In addition, other high affinity ligands may be used. Immunoassays which can be used include e.g. ELISAs, Western blots and other techniques known to those of ordinary skill in the art (see Harlow and Lane, Antibodies: A Laboratory Manual, Cold Spring Harbor Laboratory Press, Cold Spring Harbor, N.Y., 1999 and Edwards R, Immunodiagnostics: A Practical Approach, Oxford University Press, Oxford; England, 1999). All these detection techniques may also be employed in the format of microarrays, protein-arrays, antibody microarrays, tissue microarrays, electronic biochip or protein-chip based technologies (see Schena M., Microarray Biochip Technology, Eaton Publishing, Natick, Mass., 2000).

Certain diagnostic and screening methods of the present invention utilize an antibody, preferably, a monoclonal antibody, capable of specifically binding to a NCS-1-related protein as described herein or active fragments thereof. The method of utilizing an antibody to measure the levels of NCS-1 protein allows for non-invasive diagnosis of the pathological states of cancer cells, (e.g. from breast, ovarian, cervical or lung tissue). In a preferred embodiment of the present invention, the antibody is human or is humanized. The preferred antibodies may be used, for example, in standard radioimmunoassays or enzyme-linked immunosorbent assays or other assays which utilize antibodies for measurement of levels of NCS-1 protein in sample. In a particular embodiment, the antibodies of the present invention are used to detect and to measure the levels of NCS-1 protein present in a cancer sample (eg. breast, ovarian, cervical or lung cells). In the present invention, an automated quantitative analysis system or AQUA system or method (see, for example, Camp, et al., Automated subcellular localization and quantification of protein expression in tissue microarrays. *Nat Med* 2002; 8:1323-7, may be used preferably to quantify NCS-1 protein which is found in a cancer tissue sample.

Humanized antibodies are antibodies, or antibody fragments, that have the same binding specificity as a parent antibody, (i.e., typically of mouse origin) and increased human characteristics. Humanized antibodies may be obtained, for example, by chain shuffling or by using phage display technology. For example, a polypeptide comprising a heavy or light chain variable domain of a non-human antibody specific for a NCS-1 protein is combined with a repertoire of human complementary (light or heavy) chain variable domains. Hybrid pairings specific for the antigen of interest are selected. Human chains from the selected pairings may then be combined with a repertoire of human complementary variable domains (heavy or light) and humanized antibody polypeptide dimers can be selected for binding specificity for an antigen. Techniques described for generation of humanized antibodies that can be used in the method of the present invention are disclosed in, for example, U.S. Pat. Nos. 5,565,332; 5,585,089; 5,694,761; and 5,693,762. Furthermore, techniques described for the production of human antibodies in transgenic mice are described in, for example, U.S. Pat. Nos. 5,545,806 and 5,569,825.

In order to identify small molecules and other agents useful in the present methods for treating or preventing CIAE, including CIPN and/or CICAE by modulating the activity and expression of NCS-1 levels or InsP3R dependent $Ca^{2+}$ release values, NCS-1 and biologically active fragments thereof can be used for screening therapeutic compounds in any of a variety of screening techniques. Fragments employed in such screening tests may be free in solution, affixed to a solid support, borne on a cell surface, or located intracellularly. The blocking or reduction of biological activity or the formation of binding complexes between NCS-1 and the agent being tested can be measured by methods available in the art.

Other techniques for drug screening which provide for a high throughput screening of compounds affecting NCS-1 levels, or InsP3R dependent $Ca^{2+}$ release values, are known in the art. For example, microarrays carrying test compounds can be prepared, used, and analyzed using methods available in the art. See, e.g., Shalon, D. et al., 1995, International Publication No, WO95/35505, Baldeschweiler et al., 1995, International Publication No. WO95/251116; Brennan et al., 1995, U.S. Pat. No. 5,474,796; Heller et al., 1997, U.S. Pat. No. 5,605,662.

Identifying small molecules that modulate NCS-1 levels or InsP3R dependent $Ca^+$ release activity can also be conducted by various other screening techniques, which can also serve to identify antibodies and other compounds that interact with NCS-1 and can be used as drugs and therapeutics in the present methods. See, e.g., Enna et al., eds., 1998, Current Protocols in Pharmacology, John Wiley & Sons, Inc., New York N.Y. Assays will typically provide for detectable signals associated with the binding of the compound to a protein or cellular target. Binding can be detected by, for example, fluorophores, enzyme conjugates, and other detectable labels well known in the art. The results may be qualitative or quantitative.

For screening the compounds for specific binding, various immunoassays may be employed for detecting, for example, human or primate antibodies bound to the cells. Thus, one may use labeled anti-hIg, e.g., anti-hIgM, hIgG or combinations thereof to detect specifically bound human antibody. Various labels can be used such as radioisotopes, enzymes, fluorescers, chemiluminescers, particles, etc. There are numerous commercially available kits providing labeled anti-hIg, which may be employed in accordance with the manufacturer's protocol.

In one embodiment, a kit can comprise: (a) at least one reagent which is selected from the group consisting of (i) reagents that detect a transcription product of the gene coding for a NCS-1 marker as described herein (ii) reagents that detect a translation product of the gene coding for NCS-1, and/or reagents that detect a fragment or derivative or variant of said transcription or translation product; (b) instructions for diagnosing, or prognosticating cancer and/or CIAE, including chemical signaling disregulation, CIN/CIPN and/or CICAE, or determining the propensity or predisposition of a subject to develop such a disease or of monitoring the effect of a treatment by determining a level, or an activity, or both said level and said activity, and/or expression of said transcription product and/or said translation product and/or of fragments, derivatives or variants of the foregoing, in a sample obtained from said subject; and comparing said level and/or said activity and/or expression of said transcription product and/or said translation product and/or fragments, derivatives or variants thereof to a reference value representing a known disease status (patient) and/or to a reference value representing a known health status (control) and/or to a reference value; and analyzing whether said level and/or said activity and/or expression is varied compared to a reference value representing a known health status, and/or is similar or equal to a reference value representing a known disease status or a reference value; and diagnosing or prognosticating cancer and/or CIAE, including calcium signaling disregulation, CIN/CIPN and/or CICAE, or determining the propensity or predisposition of said subject to develop such a disease, wherein a varied or altered level, expression or activity, or both said level and said activity, of said transcription product and/or said translation product and/or said fragments, derivatives or variants thereof compared to a reference value representing a known health status (control) and/or wherein a level, or activity, or both said level and said activity, of said transcription product and/or said translation product and/or said fragments, derivatives or variants thereof is similar or equal to a reference value representing a known disease status (patient sample), preferably a disease status of cancer and/or CIAE, including calcium signaling disregulation, CIN/CIPN and/or CICAE, and/or to a reference value representing a known cancer and/or CIAE, including calcium signaling disregulation, CIN/CIPN and/or CICAE stage, indicates a diagnosis or prognosis of a cancer and/or CIAE, including calcium signaling disregulation, CIN/CIPN and/or CICAE stage, or an increased propensity or predisposition of developing such a disease, a high risk of developing signs and symptoms of a cancer and/or CIAE, including calcium signaling disregulation, CIN/CIPN and/or CICAE stage.

Reagents that selectively detect a transcription product and/or a translation product of the gene coding for NCS-1 can be sequences of various length, fragments of sequences, antibodies, aptamers, siRNA, microRNA, and ribozymes. Such reagents may be used also to detect fragments, derivatives or variants thereof.

These and other aspects of the invention are described further in the following non-limiting examples.

EXAMPLE 1

Drug Therapy to Prevent Chemotherapy-Induced Polyneuropathy (Repositioning of AV411 (Ibudilast))

We recently reported that paclitaxel binds to neuronal calcium sensor 1 (NCS-1) a protein found in many cell types which enhances the ability of these cells to generate internal calcium ($Ca^{+2}$) signals. B. Ehrlich, Chronic exposure to paclitaxel diminishes phosphoinositide signaling by calpain-mediated neuronal calcium sensor-1 degradation, *PNAS*, Jun. 26, 2007, vol. 104, no. 26, pp. 11103-11108. Previously it was thought that the only effect of paclitaxel was to stabilize microtubles, a structural component of cells. Our new findings provide a molecular pathway to explain paclitaxel-induced peripheral neuropathy and a potential mechanism to prevent damage of peripheral neurons.

With many chemotherapeutic drugs there is an enhanced $Ca^{+2}$ signal which leads to hyper-activation of neurons and activation of enzymes that lead to pathological changes in the neurons. Our hypothesis is that interference with these pathological cascades will avoid the negative side effect, peripheral neuropathy, associated with chemotherapeutic treatments. This work characterizes and optimizes the ability to protect isolated cells during drug exposure, thereby creating a test to evaluate drug analogs which are potentially less neurotoxic, and demonstrates the ability to protect peripheral nerves in intact animals after chemotherapeutic treatment.

Our previous studies (id.) showed the functional interactions among paclitaxel, NCS-1 and the inositol 1,4,5 trisphosphate receptor (InsP3R). We also found that addition of paclitaxel activated an enzyme, calpain, that lead to the degradation of NCS-1. We were able to prevent NCS-1 degradation by inhibiting calpain. The results from the experiments identified optimal pathway(s) to protect NCS-1 levels in cells. We tested many compounds that have the potential to protect NCS-1 levels.

First, we used analogs of paclitaxel to determine whether all compounds in this class will degrade NCS-1. Second, compounds known to inhibit the pathways identified in our published work, such as calpain inhibitors, were tested and optimized. Third, other potentially therapeutic compounds, such as compounds that mimic the sensitive portion of NCS-1 so that the activity of calpain can be diverted to a different target, were tested. The results from these experiments guide in vivo testing.

More specifically, AV411 (ibudilast) is a drug used in several Asian countries for treatment of bronchial asthma, cerebrovascular disorders, post-stroke dizziness, and ocular allergies. In accordance with the Materials and Methods section of *PNAS*, Jun. 26, 2007, vol. 104, no. 26, pp. 11103-11108, supra, rats were co-administered paclitaxel and AV411 and the following observations were made.

Figure 1A:
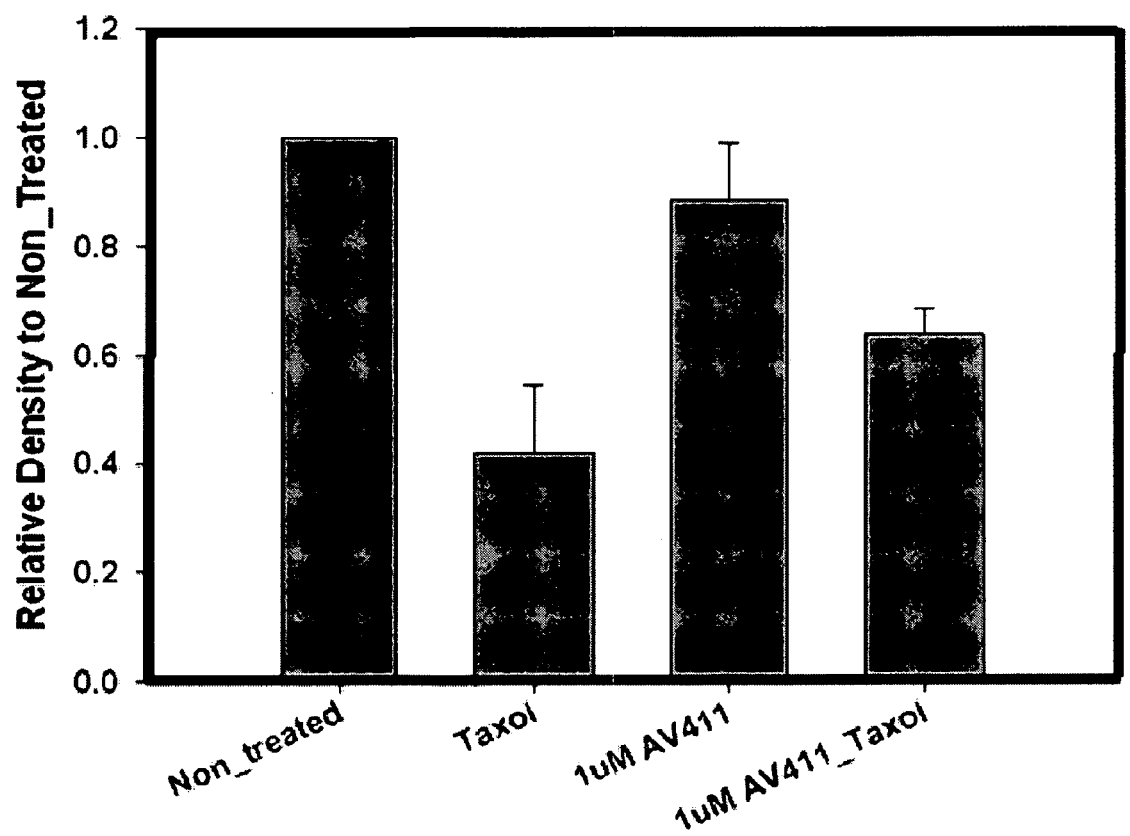
FIG. 1A: AV411 (ibudilast) protects NCS-1 degradation by Taxol. Western blot analysis reveals that Taxol treatment (800 ng/mL, 6 hours) decreases NCS-1 levels (bar 2). The addition of 1 uM AV411 alone did not significantly decrease NCS-1 levels (bar 3). The combination of AV411 with Taxol appears to partially protect against Taxol-induced reduction in NCS-1 levels (bar 4). Data shown are the average of three experiments.
Figure 1B:
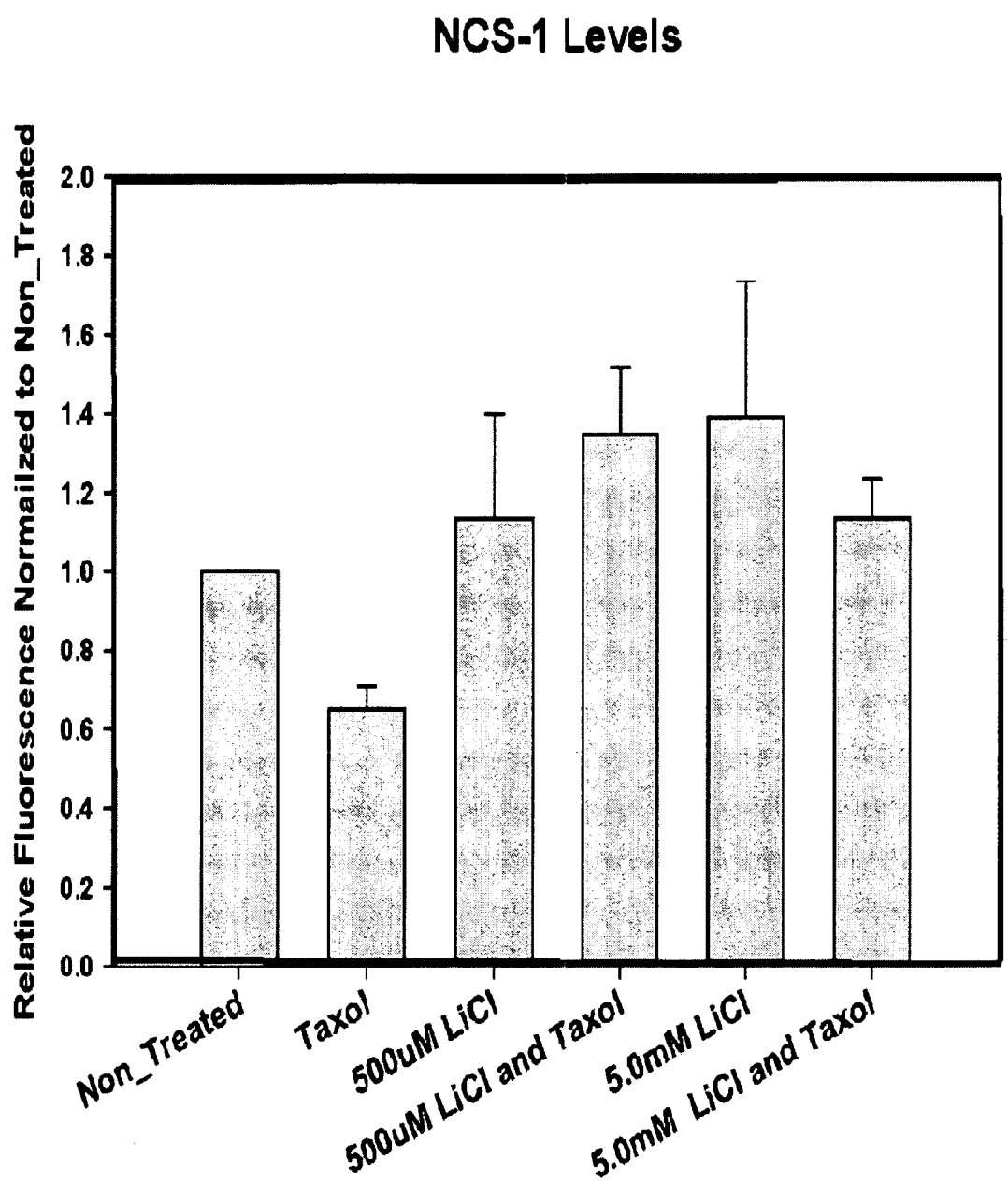
FIG. 1B: Lithium chloride (LiCl) protects NCS-1 degradation by Taxol. Western blot analysis reveals that Taxol treatment (800 ng/mL, 6 hours) decreases NCS-1 levels (bar 2). The addition of 500 uM or 5.0 mM LiCl alone did not decease NCS-1 levels (bars 3 and 5). However, the combination of LiCl with Taxol prevents Taxol-induced reduction in NCS-1 levels (bars 4 and 6). Data shown are the average of three experiments.

As shown in FIG. 1A, AV411 (ibudilast) protected NCS-1 degradation by paclitaxel. Western blot analysis revealed that paclitaxel treatment (800 ng/mL, 6 hours) decreased NCS-1 levels (bar 2). The addition of 1 uM AV411 alone did not significantly decrease NCS-1 levels (bar 3). The combination of AV411 with paclitaxel appears to partially protect against paclitaxel-induced reduction in NCS-1 levels (bar 4). Data shown are the average of three experiments.

Figure 2:
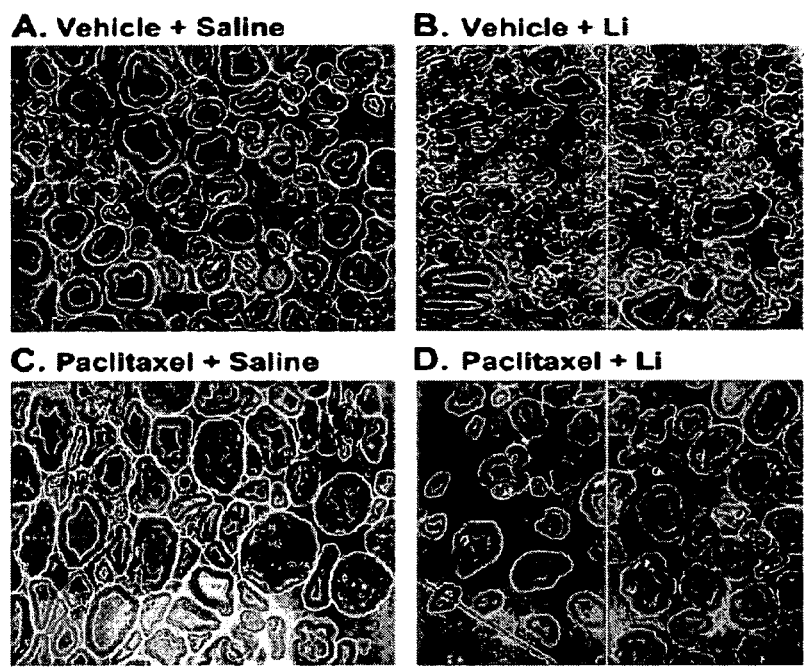
FIG. 2: Lithium protects mice from paclitaxel-induced damage; evident myelin damage enlarged structures.
Figure 2A:
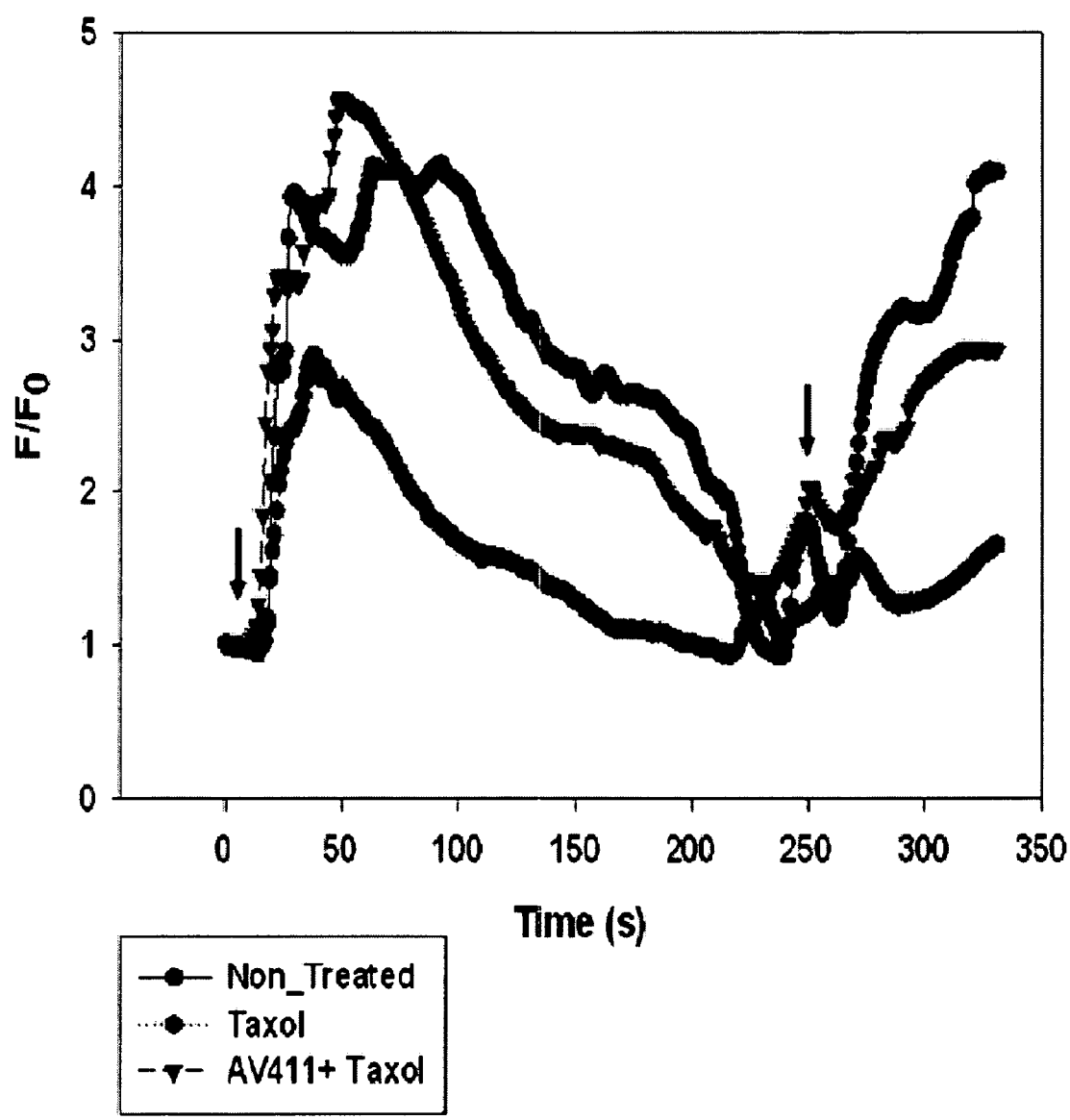
FIG. 2A: Protection of the intracellular calcium signal by 1 uM AV411. Representative $Ca^{2+}$ responses of SHSY-5Y cells stimulated with 1 uM ATP (at first arrow) to induce a transient release of $Ca^{2+}$ from intracellular stores. After 200 seconds thapsigargin (TG, an inhibitor of the intracellular $Ca^{2+}$ pump) was added to indicate that the intracellular stores were filled and the cells were viable (second arrow). Cells treated with 800 ng/mL Taxol for 6 hours (blue trace) had a response lower in amplitude than non-treated cells (black trace). Addition of 1 uM AV411 to cells during taxol treatment prevented the reduction in signaling (purple trace). Each line represents the average of at least 45 cells (at least 15 cells measured in three separate experiments).

Also, as shown in FIG. 2A, we observed protection of the intracellular $Ca^{2+}$ signal by 1 uM AV411. Representative $Ca^{2+}$ responses of SHSY-5Y cells stimulated with 1 uM ATP (at first arrow) to induce a transient release of $Ca^{2+}$ from intracellular stores. After 200 seconds thapsigargin (TG, an inhibitor of the intracellular $Ca^{2+}$ pump) was added to indicate that the intracellular stores were filled and the cells were viable (second arrow). Cells treated with 800 ng/mL Taxol for 6 hours (blue trace) had a response lower in amplitude than non-treated cells (black trace). Addition of 1 uM AV411 to cells during taxol treatment prevented the reduction in signaling (purple trace). Each line represents the average of at least 45 cells (at least 15 cells measured in three separate experiments).

EXAMPLE 2

Drug Therapy to Prevent Chemotherapy-Induced Polyneuropathy (Repositioning of Li Salt and Other Agents)

In the experiment of this example, we found that all three classes of drugs that treat bipolar disease (lithium carbonate, valproic acid, and chlorpromazine) prevent neuronal calcium sensor 1 (NCS-1) from binding to the inositol 1,4,5 trisphosphate receptor (InsP3R). Based upon our observations regarding the activity of lithium carbonate, valproic acid, and chlorpromazine, we believe that there are additional drugs in these classes that will have the desired effect of preventing chemotherapy-induced polyneuropathy such as, but not limited to, bortezomib and carfilzomib.

Figure 9:
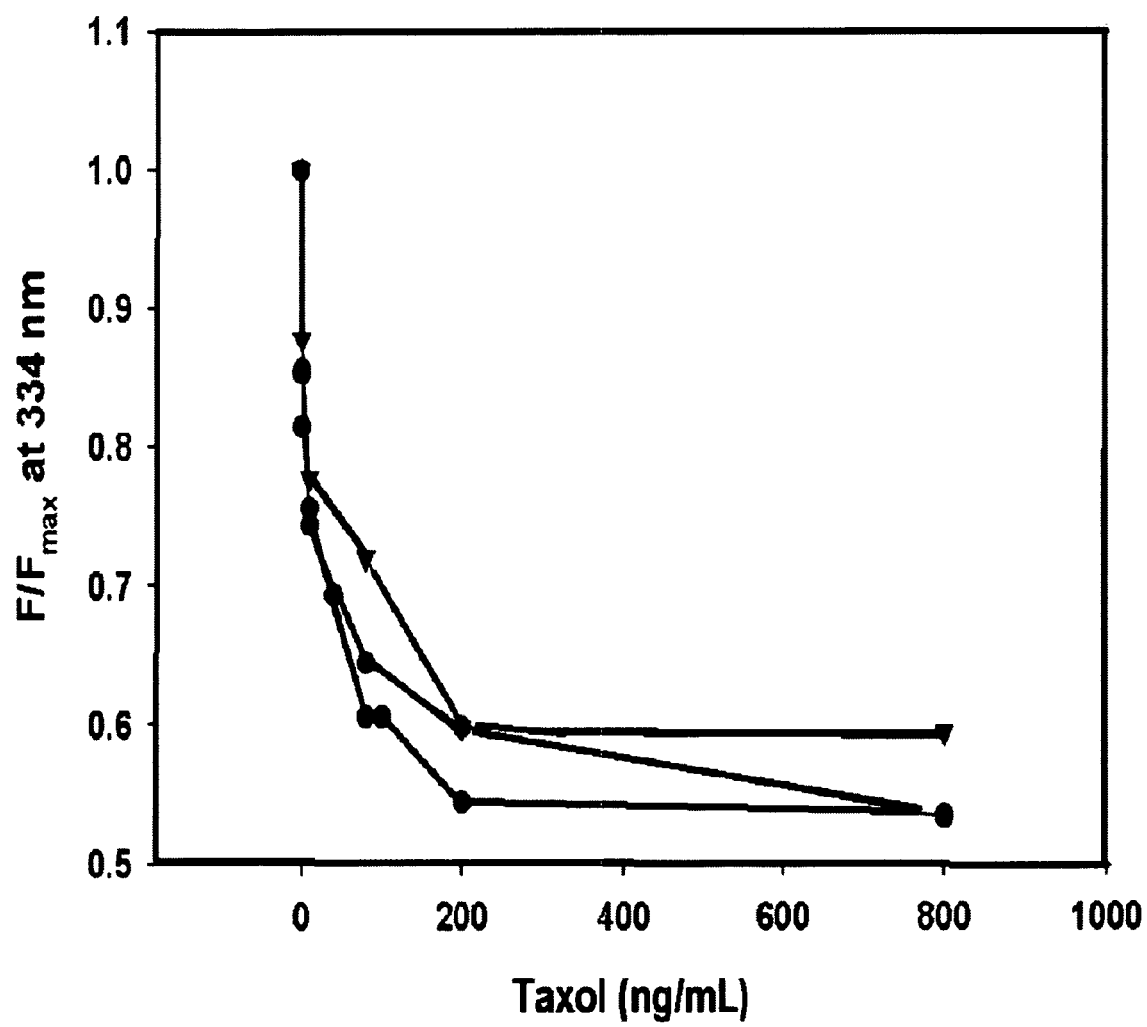
FIG. 9: Tryptophan fluorescence confirms that paclitaxel binds to NCS-1.
Figure 10:
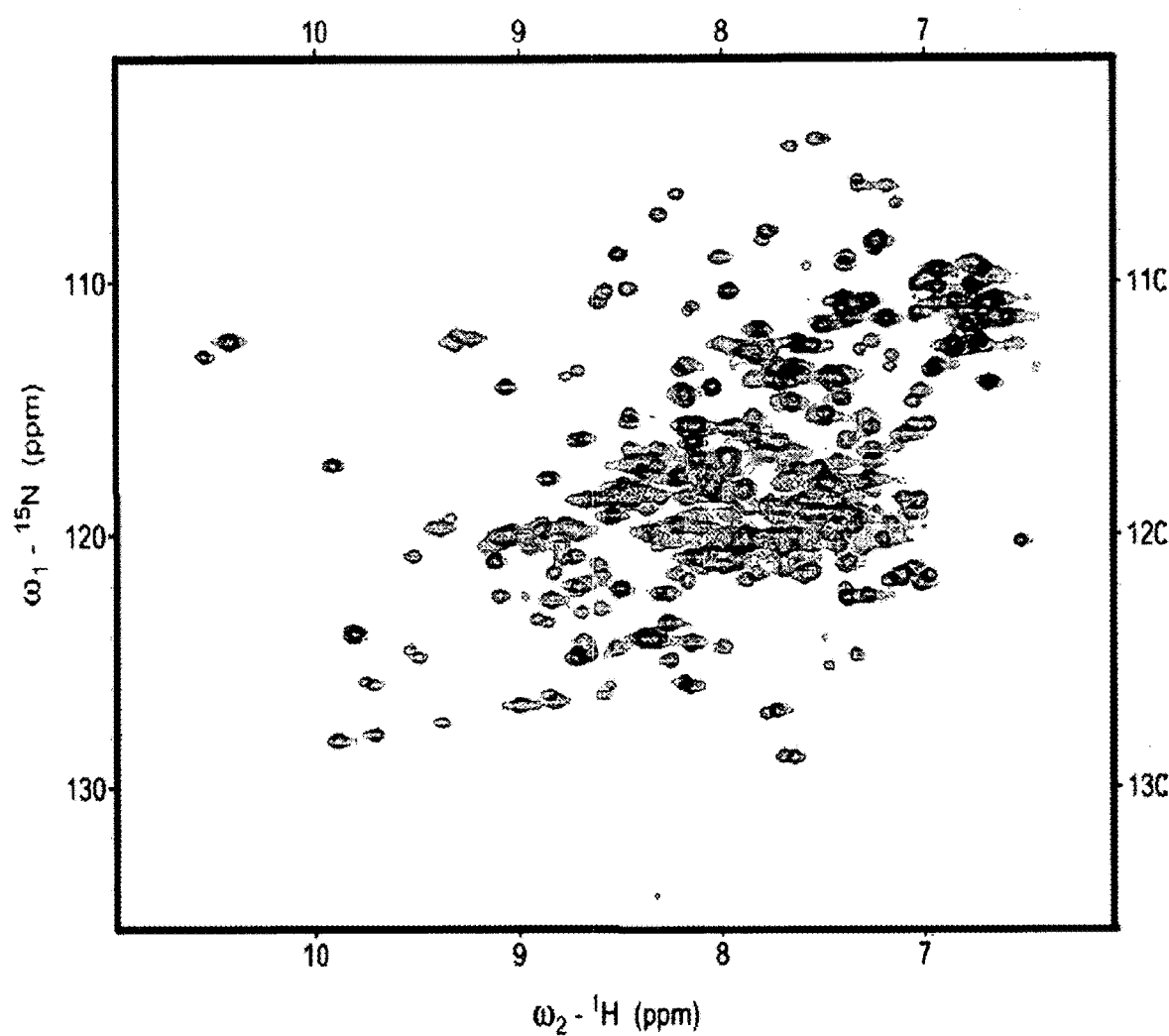
FIG. 10: NMR confirms Ibudilast binding to NCS-1.

The relative effects of paclitaxel-LiCl and paclitaxel-AV411 co-administration on microtubule assembly were also determined. Additionally, we confirmed through tryptophan fluorescence that paclitaxel binds to NCS-1 (FIG. 9). NMR confirmed that AV411 (ibudilast) binds to NCS-1 (FIG. 10).

These bipolar drugs only prevent the NCS-1 dependent activity of the InsP3R. This NCS-1 dependent activity is an early step in the production of peripheral neuropathy. By adding the bipolar drugs to cancer treatment one can prevent the neurological side-effects of certain chemotherapies (adjunct therapy and/or co-administration and/or formulation, etc.).

In accordance with the Materials and Methods section of *PNAS*, Jun. 26, 2007, vol. 104, no. 26, pp. 11103-11108, supra, mice were co-administered paclitaxel and lithium carbonate, valporic acid, chlorpromazine and in some instances AV411 and the following observations were made.

Figure 13:
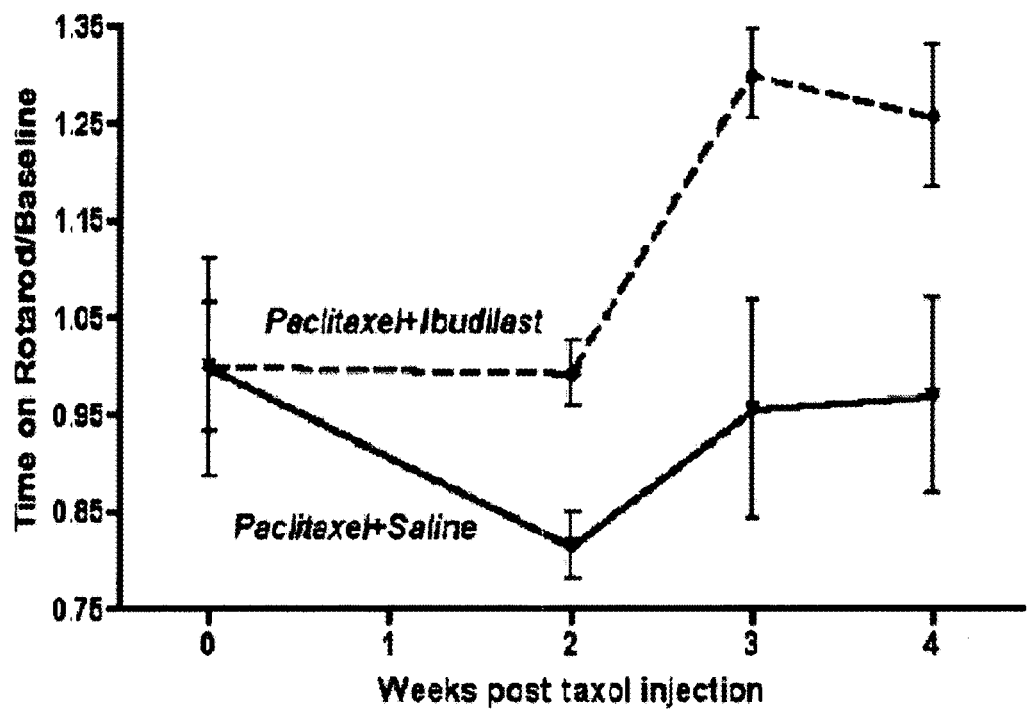
FIG. 13: Ibudilast protects mice from developing neuropathy; 5 mice/group; paclitaxel 4.5 mg/kg per ip injection, 4 injections Ibudilast 10 mg/kg ip injection 1 hour prior to paclitaxel.
Figure 13:
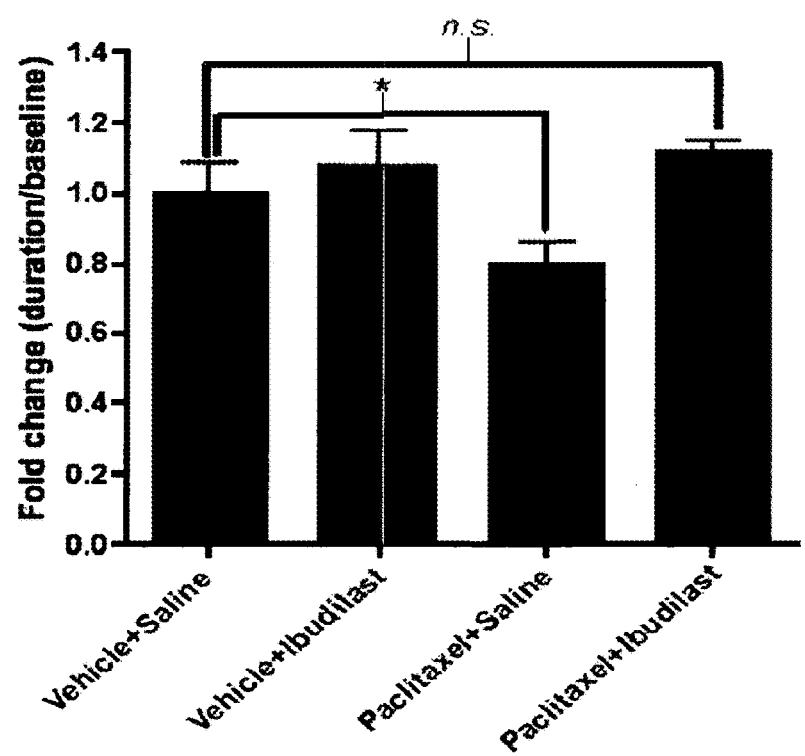

As shown in FIG. 13, there is NCS-1 degradation in neuroblastoma cells (SHSY-5Y) treated with Taxol for 6 hours (compare first and second bars). NCS-1 levels were found to be protected from the Taxol-induced degradation of NCS-1 in the presence of 500 uM and 5.0 mM lithium chloride (LiCl) (compare bar 2 in the presence of Taxol alone, with bars 4 and 6 which show treatment with Taxol and LiCl). Treatment with LiCl alone did not reduce NCS-1 levels (compare bar 1 without LiCl to bars 3 and 5 with LiCl alone). These data show that the addition of LiCl in the presence of Taxol treatment allows cells to maintain NCS-1 levels.

Figure 3:
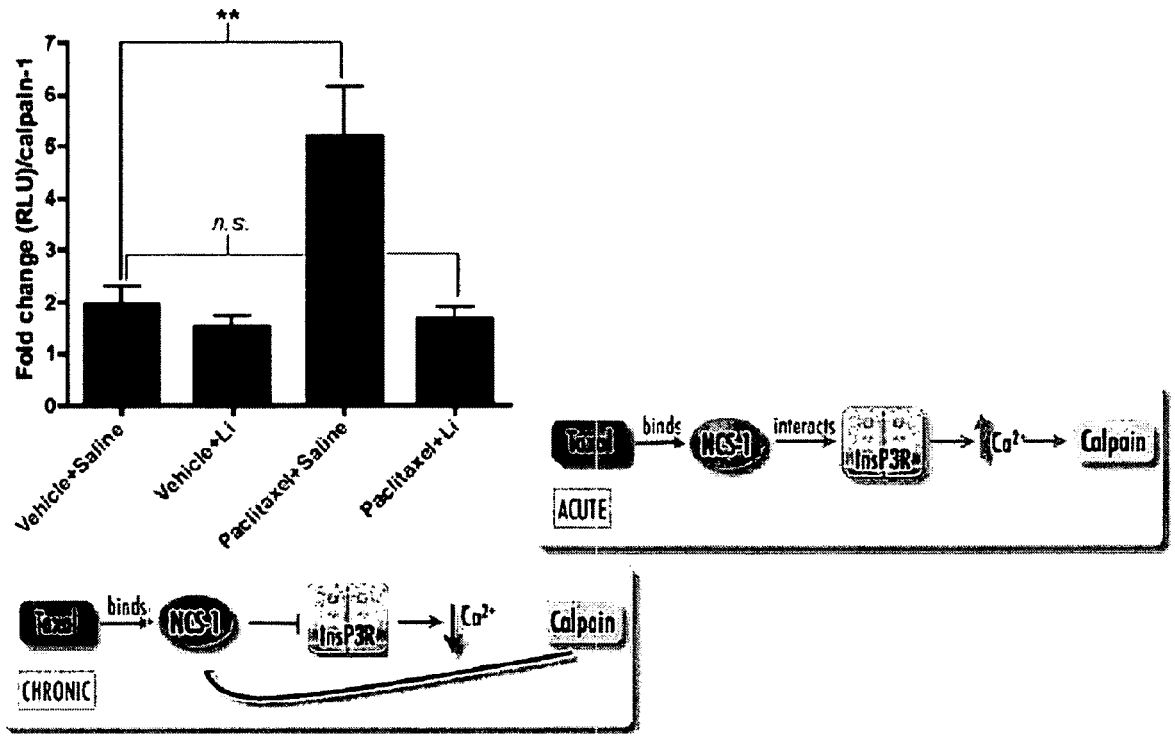
FIG. 3: Low dose paclitaxel increases calpain activity. Lithium treatment prevents activation of calpain.
Figure 2B:
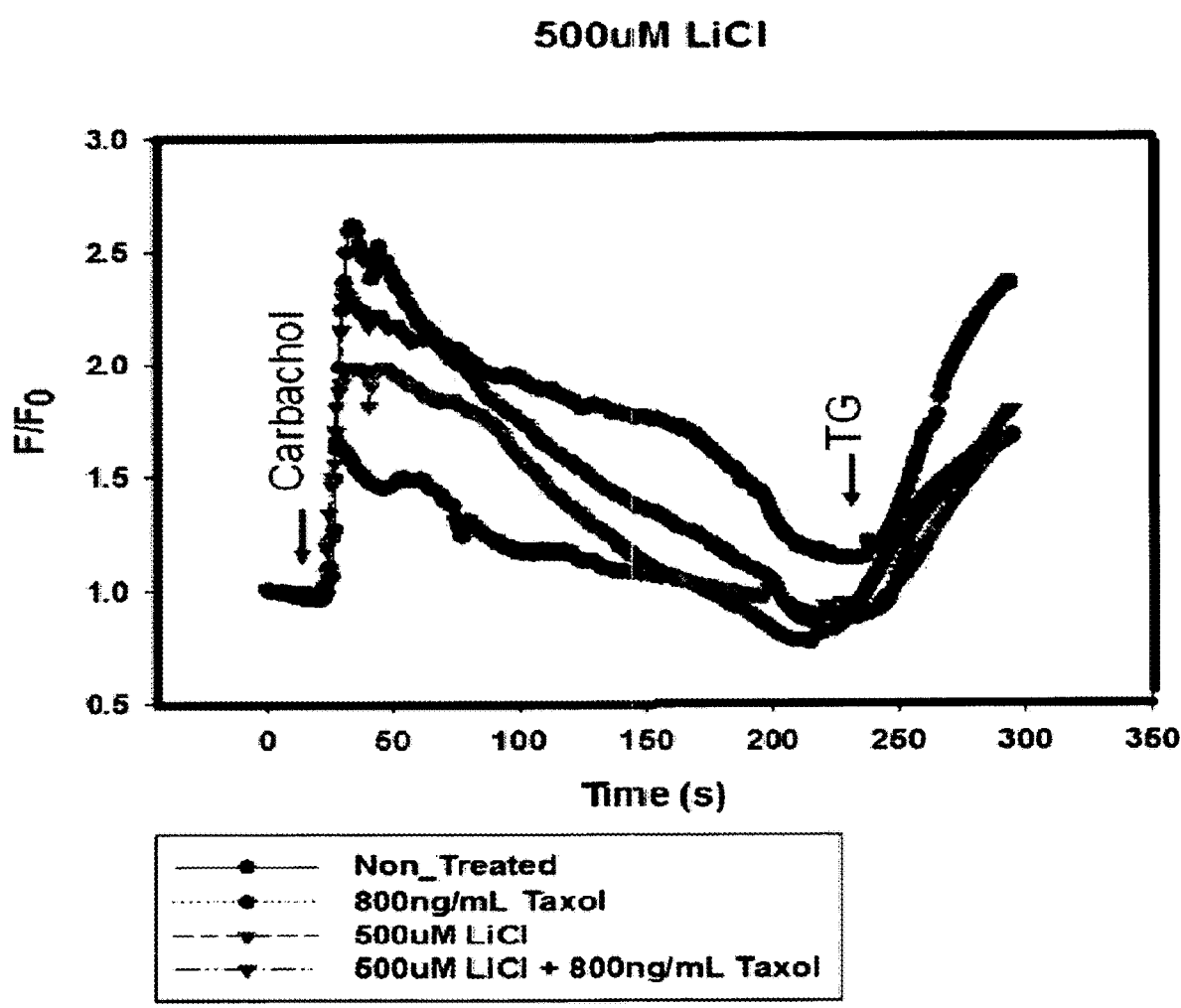
FIG. 2B: Protection of the intracellular calcium signal by 500 uM LiCl. Representative $Ca^{2+}$ responses of SHSY-5Y cells stimulated with 200 nM carbachol (at first arrow) to induce a transient release of $Ca^{2+}$ from intracellular stores. After 200 seconds thapsigargin (TG, an inhibitor of the intracellular $Ca^{2+}$ pump) was added to indicate that the intracellular stores were filled and the cells were viable (second arrow). Cells treated with 800 ng/mL Taxol for 6 hours (blue trace) had a response lower in amplitude and shorter in duration that non-treated cells (black trace). Addition of 500 uM LiCl alone (pink trace)induced a small decrease in the $Ca^{2+}$ transient. However, the addition of 500 uM LiCl to cells, during Taxol treatment prevented the reduction in signaling (maroon trace). Each line represents the average of at least 45 cells (at least 15 cells measured in three separate experiments).
Figure 3B:
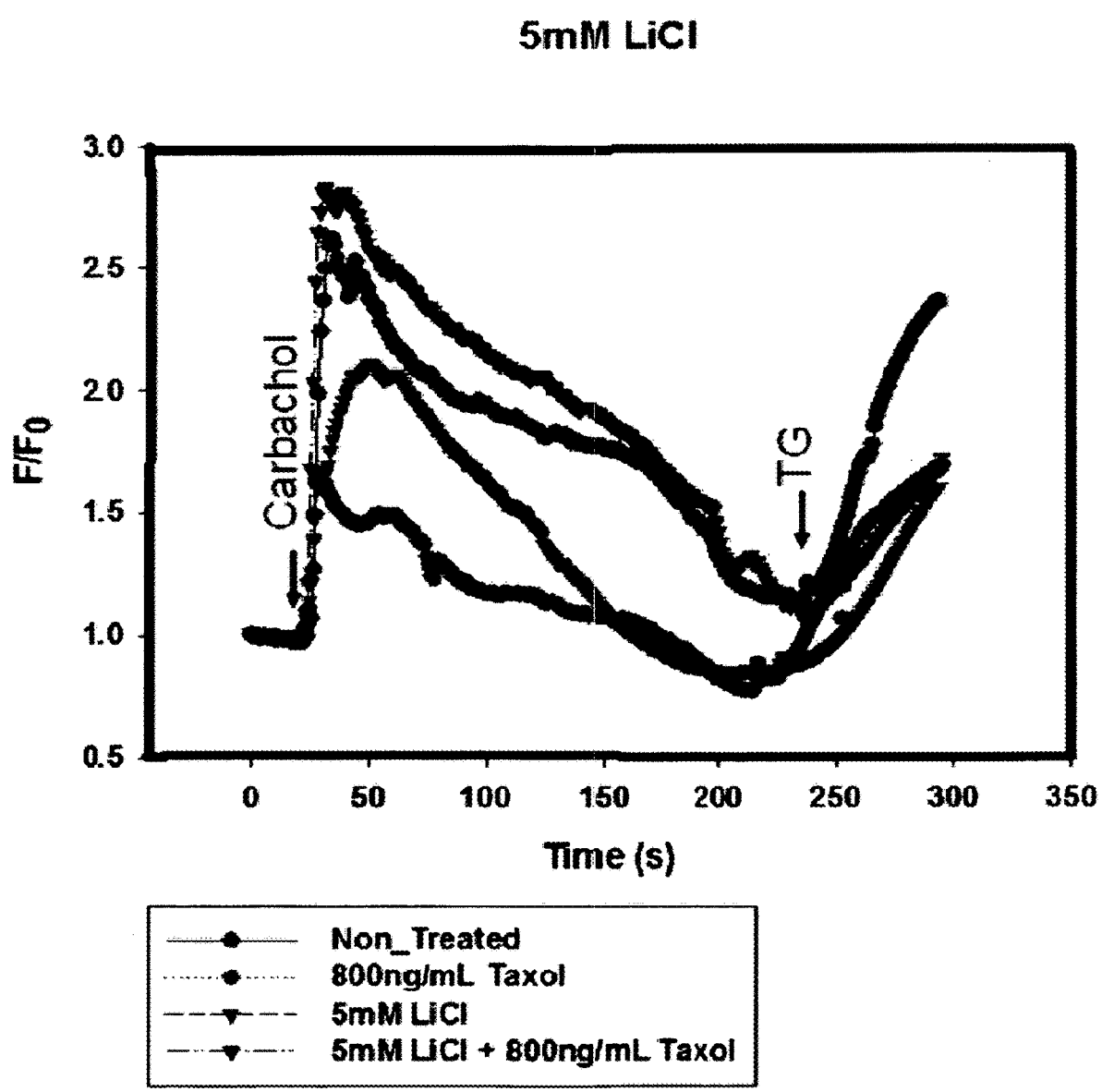
FIG. 3B: Protection of the intracellular calcium signal by 5.0 mM LiCl. Representative $Ca^{2+}$ responses of SHSY-5Y cells treated with 800 ng/mL Taxol for 6 hours in the presence and absence of 5.0 mM. The experiment is the same as described for FIG. 2 except that 5 mM LiCl was used.

Intracellular $Ca^{2+}$ signals monitored in intact cells were also found to be reduced by treatment with Taxol for 6 hours (FIGS. 2B and 3B; compare control treatment (black trace) with Taxol treatment (blue trace) in both figures). Cells treated with 500 uM (FIG. 2B, maroon trace) or 5.0 mM LiCl (FIG. 3, brown trace) in the presence of Taxol responded to stimulation with $Ca^{2+}$ signals similar to that of non-treated cells. Treatment with LiCl alone decreased the intracellular signals, but not to the extent seen with Taxol treatment (FIG. 2B pink trace and FIG. 3D, red trace). These data show that the addition of LiCl in the presence of Taxol treatment protects intracellular $Ca^{2+}$ signals as well as NCS-1 levels (FIGS. 2B and 3B).

We found that in the absence of LiCl the binding of NCS-1 to the InsP3R enhances intracellular $Ca^{2+}$ signals. The addition of this bipolar drug only prevents the NCS-1 dependent component of the InsP3R. We believe that this NCS-1 dependent activity is an early step in the cascade leading to the production of peripheral neuropathy. The results included here show that addition of LiCl in the presence of prolonged exposure to Taxol protects NCS-1 levels and intracellular $Ca^{2+}$ signals in the cell. This ability to maintain NCS-1 levels and NCS-1 dependent signaling should prevent Taxol-induced damage to the nerves. By adding this particular drug already used to treat bipolar disease to existing cancer treatments, we believe that peripheral neuropathy can be inhibited or in certain eases, even prevented.

Figure 4:
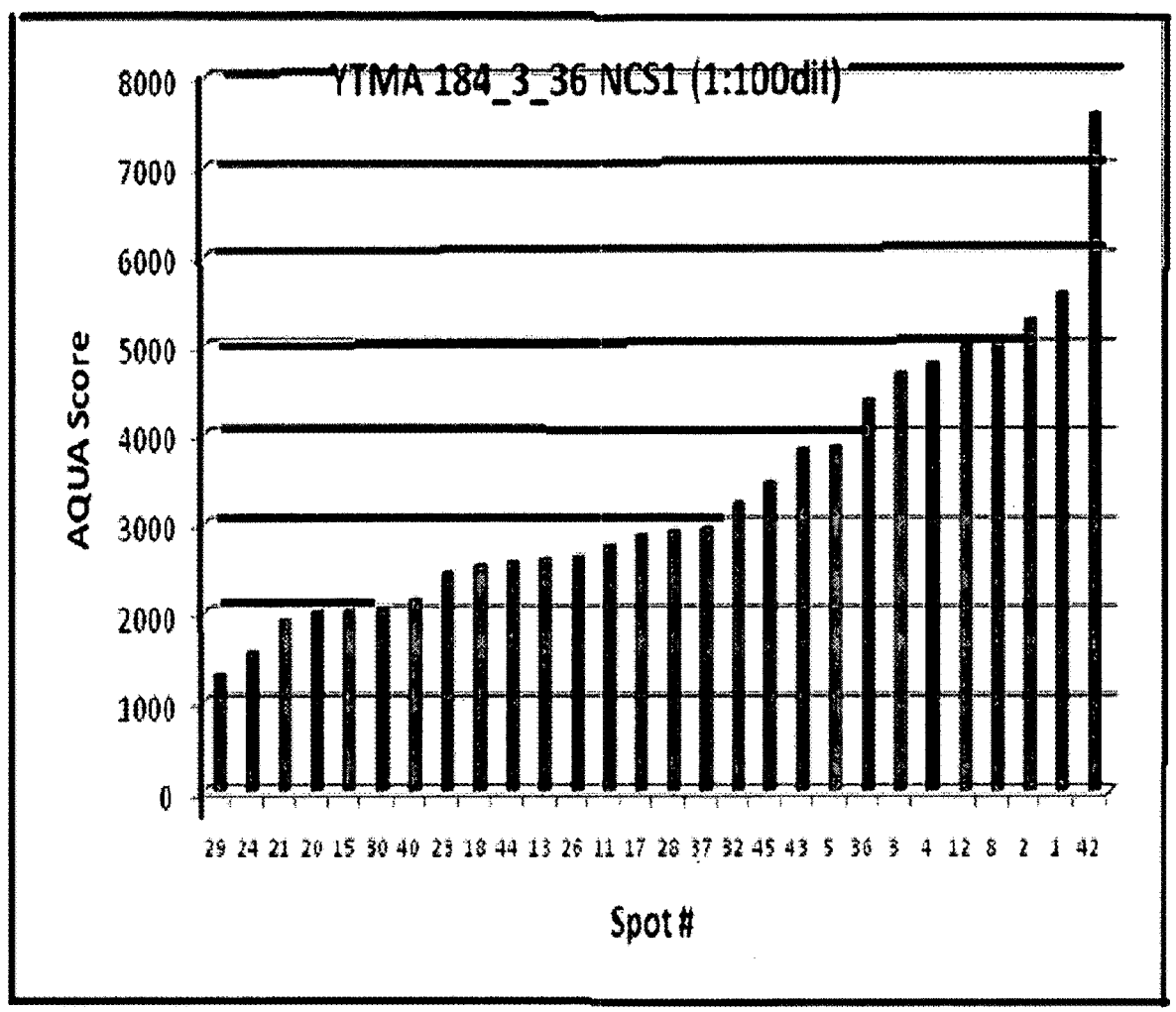
FIG. 4: Expression of NCS-1 varies in human breast tissue samples.
Figure 4B:
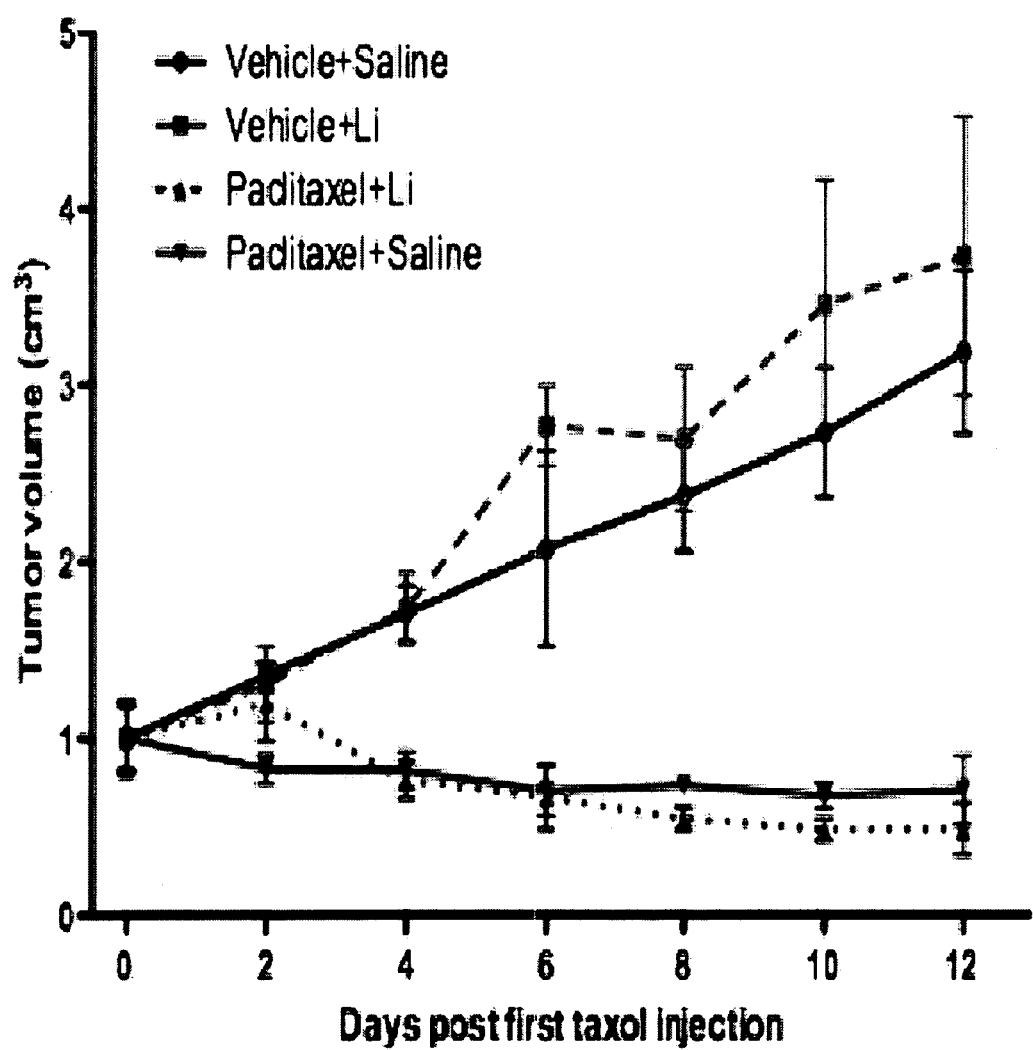
FIG. 4B: tumor volume effect.

FIG. 4B also demonstrates that not only does the addition of LiCl in the presence of Taxol treatment allow cells to maintain NCS-1 levels, it also allows a statistically significant decrease in tumor volume in a relatively short time after initiation of co-therapy.

Further, the data of FIG. 1 provide in vivo evidence that lithium protects mice from developing neuropathy (as indicated by increased mouse time on rotarod). (10 mice/group; paclitaxel 4.5 mg/kg per ip injection, 4 injections lithium 12.8 mg/kg ip injection 1 hour prior to paclitaxel.) FIG. 2 evidences that lithium protected the mice from paclitaxel-induced damage (there was evident myelin damage enlarged structures in the samples taken from paclitaxel-treated mice which did not receive Li-cotherapy). It was also noted, as presented in FIG. 4, that low dose paclitaxel increased calpain activity. Lithium treatment was found to prevent activation of calpain.

Figure 5:
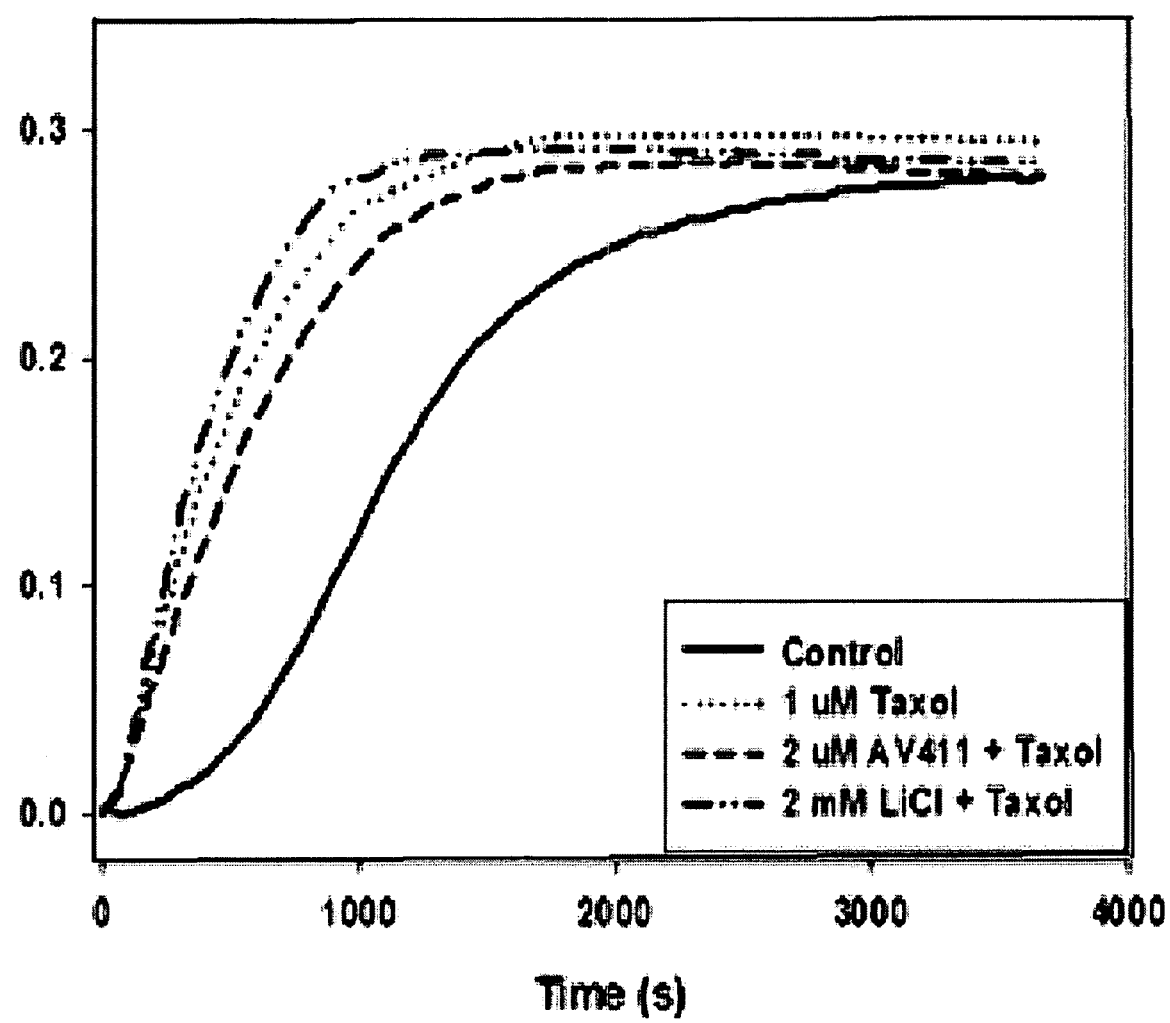
FIG. 5: Paclitaxel speeds up microtubule assembly. Neither lithium nor ibudilast alter microtubule assembly.

The results presented in FIG. 5 indicate that paclitaxel accelerates microtubule assembly, whereas neither lithium nor ibudilast alter microtubule assembly.

Figure 6:
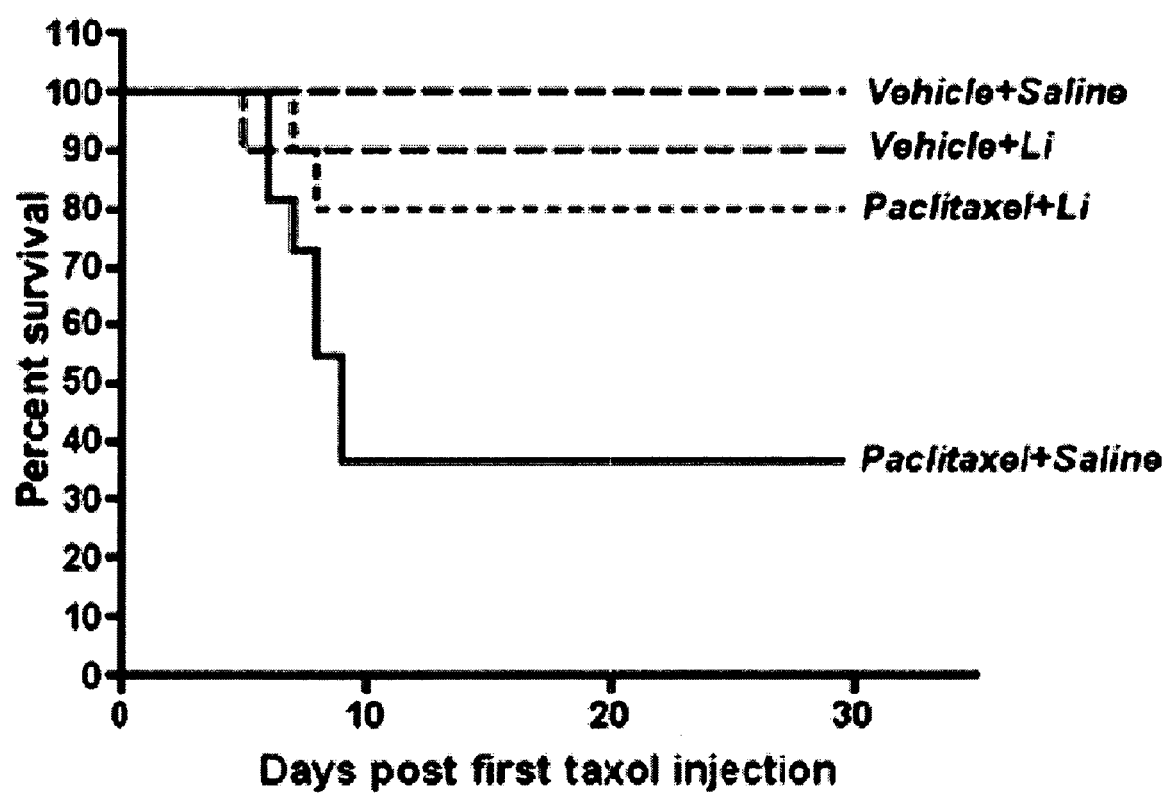
FIG. 6: High doses of paclitaxel are toxic. Lithium protects mice against toxic effects. 10 mice/group; paclitaxel 30 mg/kg per ip injection, 4 injections Lithium 12.8 mg/kg ip injection 1 hour prior to paclitaxel.
Figure 7:
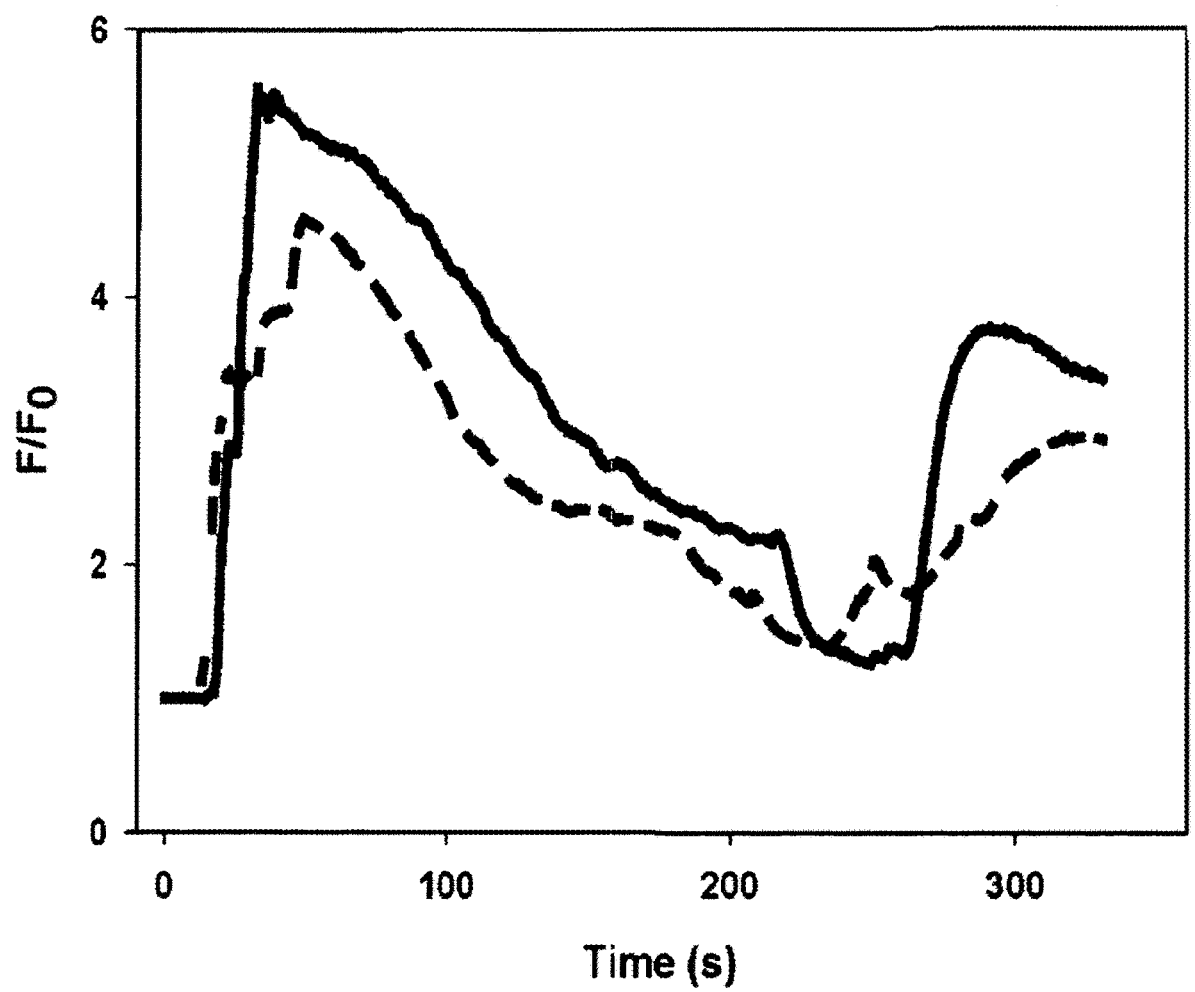
FIG. 7: Combination treatment protects calcium signaling.
Figure 8:
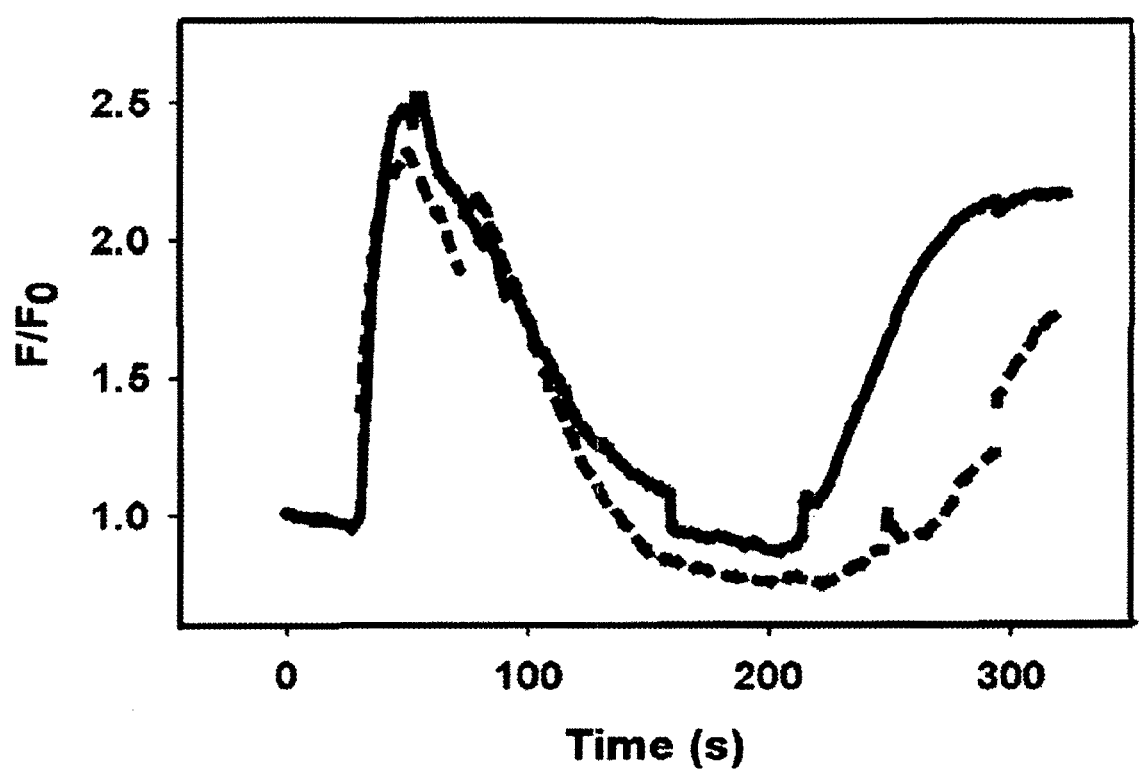
FIG. 8: Expression of calpastatin, a natural calpain antagonist, protects calcium signaling in cells.

High doses of paclitaxel proved to be toxic, as shown in FIG. 6. However, lithium protected the mice against toxic effects. (10 mice/group; paclitaxel 30 or 60 mg/kg per ip injection, 4 injections Lithium 12.8 mg/kg ip injection 1 hour prior to paclitaxel.) Combination treatment with Li and calpastatin, a natural calpain antagonist, also protected calcium signaling, as depicted in FIGS. 7 and 8.

Figure 11:
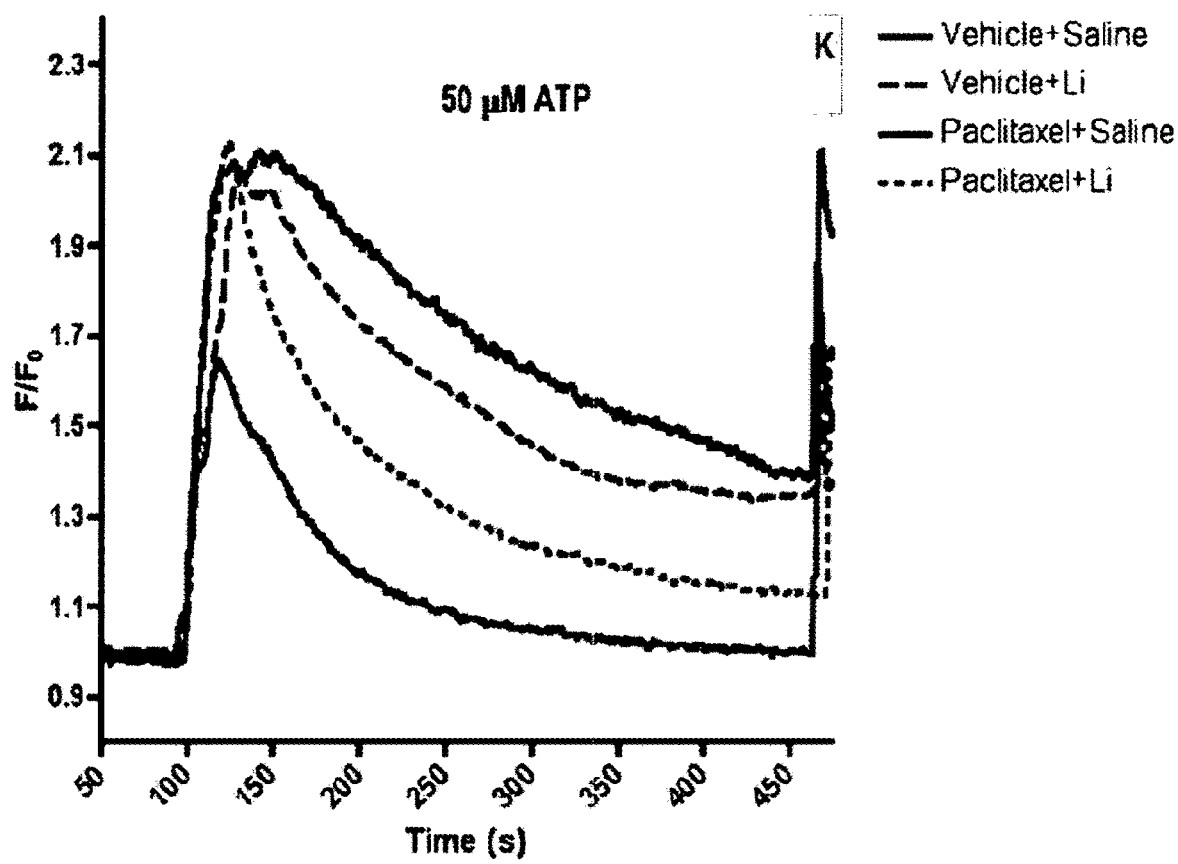
FIG. 11: Low dose paclitaxel decreases calcium release Lithium treatment prevents loss of calcium release.
Figure 11:
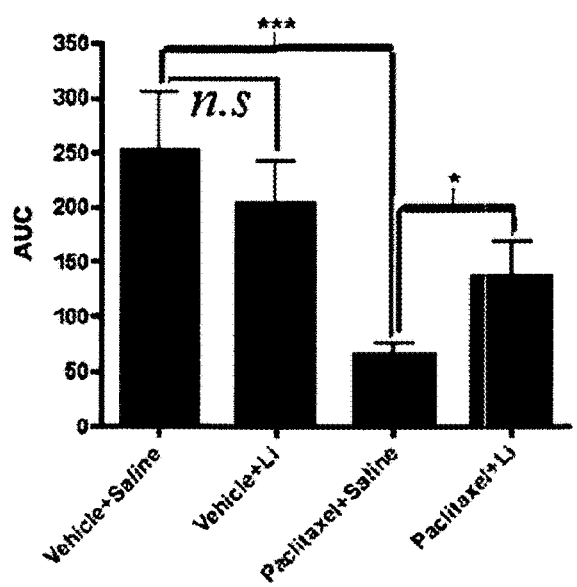
Figure 12:
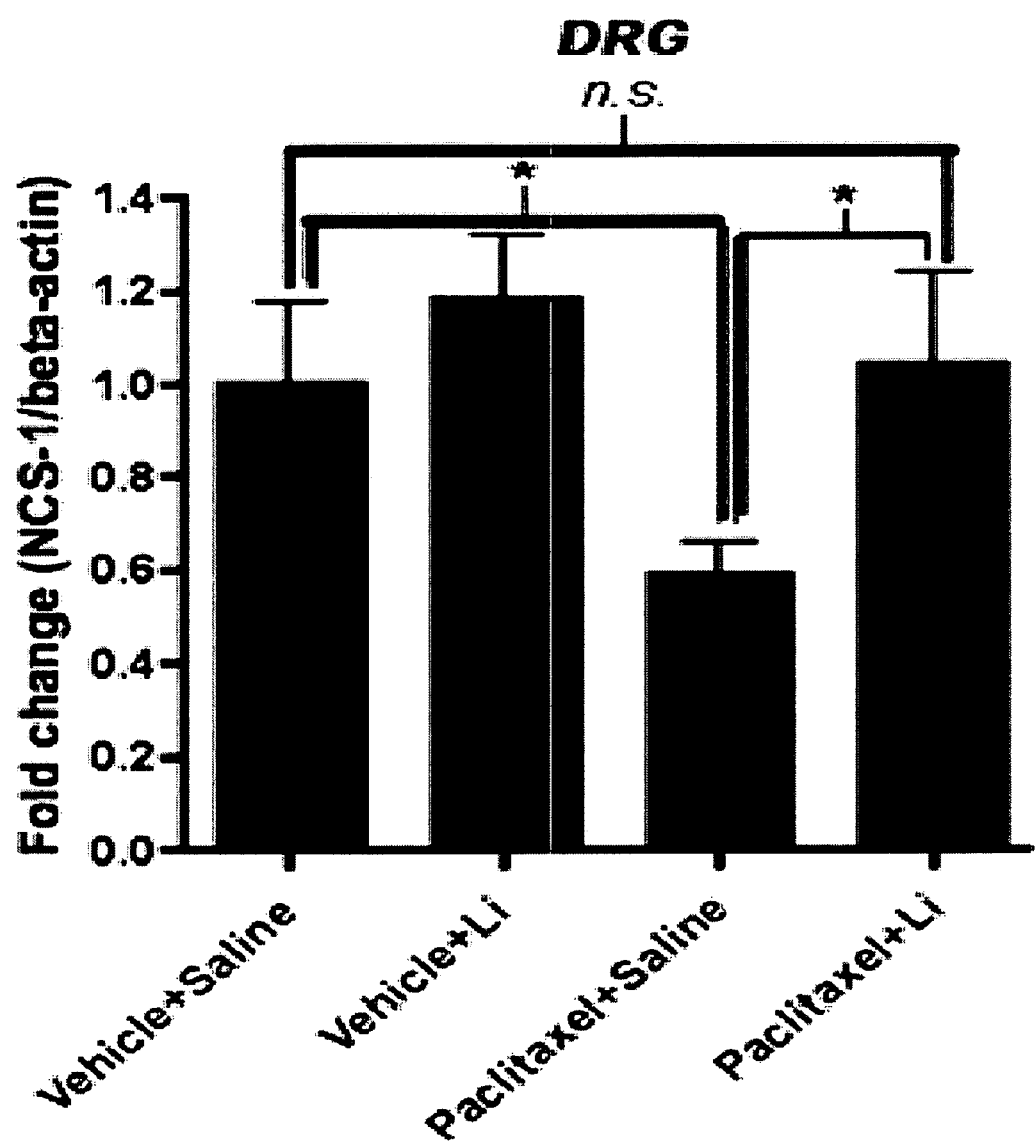
FIG. 12: Low dose paclitaxel decreases NCS-1 levels in peripheral nerve, but not brain NCS-1 expression is maintained with lithium.

Interestingly, it was observed that low doses of paclitaxel decreased calcium release and that lithium treatment prevented loss of calcium release (FIG. 11). Further, low dose paclitaxel decreased NCS-1 levels in peripheral nerve, but not in the brain (because taxol does not cross the blood brain barrier). In contrast, NCS-1 expression was maintained with lithium (FIG. 12). The data shown in FIG. 13 confirmed that ibudilast protected mice from developing neuropathy (5 mice/group; paclitaxel 4.5 mg/kg per ip injection, 4 injections ibudilast 10 mg/kg ip injection 1 hour prior to paclitaxel).

EXAMPLE 3

Expression of NCS-1 in Human Breast Tissue

We used an automated scoring system for assessing biomarker expression in tissue sections called the automated quantitative analysis (AQUA) system (JNCI *J Natl Cancer Inst* (21 Dec. 2005) 97 (24): 1808-1815, see also, Camp, et al., *Nat Med* 2002; 8:1323-7) to evaluate NCS-1 expression in human breast tissue. The AQUA system is linked to a fluorescent microscope system that detects the expression of biomarker proteins by measuring the intensity of antibody-conjugated fluorophores within a specified subcellular compartment (typically including the nucleus, cytoplasm, and plasma membrane) within the tumor region of each tissue microarray spot. The result is a quantitative score of immunofluorescence intensity for the tumor. The use of an AQUA analysis method removes the subjectivity of the traditional scoring system and provides more continuous and reproducible scoring of protein expression scoring in tissue samples. Id.

As shown in FIG. 4, expression of NCS-1 was found to vary in human breast tissue samples. This data was obtained using the following experimental protocol. To detect expression in human breast tissue, the inventors used a commercially available slide (Yale Breast Cancer Cohort YTMA-184) with approximately 120 samples from breast cancer tumors.

EXAMPLE 4

Breast Cancer Xenograph Experiment

Overview
Series 1:
Independent study to show that protector drugs do not alter efficacy of chemotherapeutics
Groups: Vehicle for paclitaxel
Paclitaxel
Paclitaxel plus lithium
lithium
10 mice per group (4 groups), to monitor tumor growth, harvesting of nerve tissues for pathology and biochemistry.

One or more murine models as described in Richmond, et al., Mouse xenograft models vs GEM models for human cancer therapeutics, *Dis Model Mech.* 2008 September-October; 1(2-3): 78-82, are prepared. As explained by Richmond, et al., "[t]hese models are used to investigate the factors involved in malignant transformation, invasion and metastasis, as well as to examine response to therapy. One of the most widely used models is the human tumor xenograft. In this model, human tumor cells are transplanted, either under the skin or into the organ type in which the tumor originated, into immunocompromised mice that do not reject human cells. For example, the xenograft will be readily accepted by athymic nude mice, severely compromised immunodeficient (SCID) mice, or other immunocompromised mice (Morton and Houghton, 2007). Depending upon the number of cells injected, or the size of the tumor transplanted, the tumor will develop over 1-8 weeks (or in some instances 1-4 months, or longer), and the response to appropriate therapeutic regimes can be studied in vivo."

Pursuant to the above protocol, a lung cancer cell line (H1975) was injected into nude mice; after two weeks tumors were large enough to measure. Exemplary dosages for use in the above murine models include 25 mg/kg taxol injected 1 time per week (2×), lithium (12.8 mg/kg) injected 1 hour prior to paclitaxel injection. Protection of NCS-1 levels and intracellular $Ca^{2+}$ signals in cells is evaluated using techniques as described in Examples 1-3.

EXAMPLE

Cardiovascular Effects

Figure 5B:
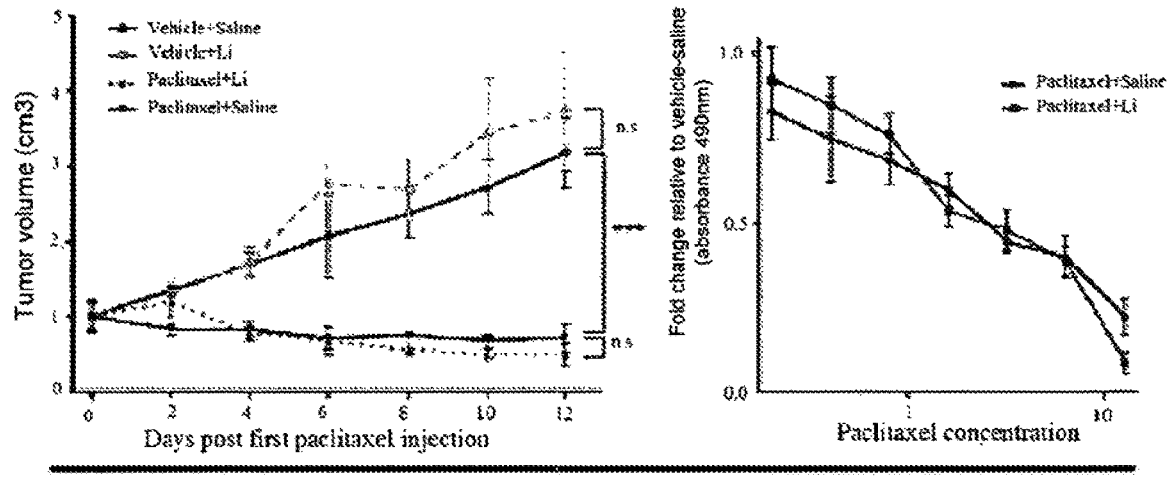
FIG. 5B: The bottom three panels of the figure attached, is from echocardiograms done on mice injected with taxol. These are the same mice for which the xenograph study was done (shown at the top of the figure). The inventors found end diastolic diameter and fractional shortening were altered 1 hour after taxol injection. These are both measurements of contractility. Lithium pre-treatment returns the values to control levels. Heart rate was not altered.
Figure 5B:
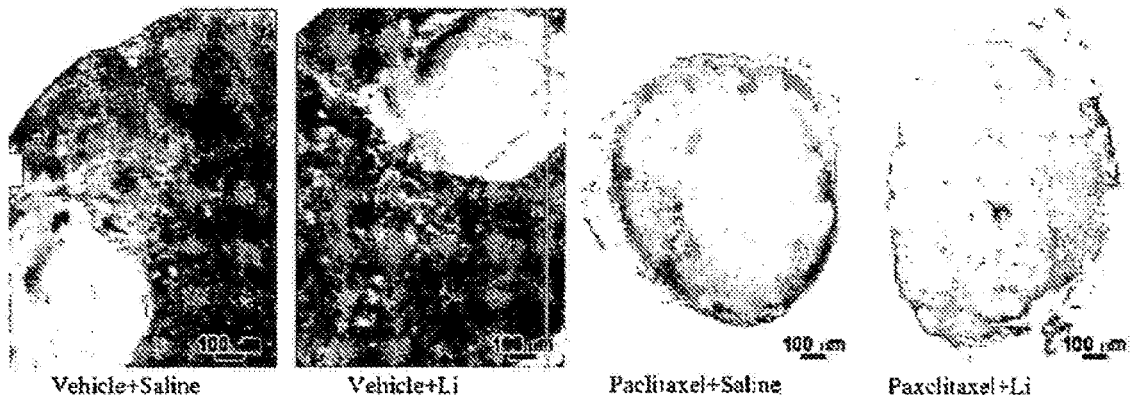
Figure 5B:
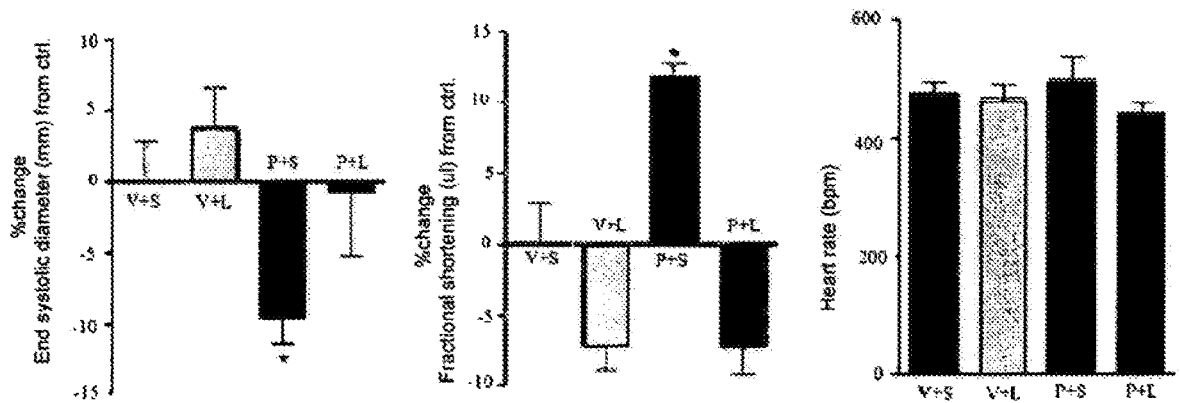

Taxol causes cardiac arrhythmias. Zhang, et al., *Journal of molecular and cellular cardiology* 49, 829-835 (2010) shows that NCS-1 is increased in cardiomyocytes and this causes increased calcium signaling. The recent data shown in the bottom three panels of the FIG. 5B, is information compiled from echocardiograms done on mice injected with taxol. These are the same mice upon which the xenograph study was done (shown at the top of the figure). The experiment found that end diastolic diameter and fractional shortening were altered 1 hour after taxol injection. These are both measurements of contractility, which was reversed by lithium pre-treatment. In particular and unexpectedly, lithium pre-treatment returns the values to control levels. Heart rate was not altered. The cardiologist who performed the experiment at the request of the inventor(s) was quite impressed and is considering studies in human patients. There are studies in the literature showing that chemotherapy induced changes acutely in contractility can develop into long term heart rhythm problems.

The invention claimed is:

1. A method of treatment comprising inhibiting, reducing the likelihood of the onset of or ameliorating central nervous system effects of reduced cognition/cognitive impairment in a patient in need caused by the administration of an anti-cancer active agent by co-administering to the patient a pharmaceutically effective amount of lithium, wherein the anti-cancer active agent is a taxane, a *vinca* alkaloid or a mixture thereof.

2. The method according to claim 1 wherein said taxane is selected from the group consisting of paclitaxel, docetaxel, IDN 5390 (13-(N-Boc-3-i-butylisoserinoyl)-C-7,8-seco-10-deacetylbaccatin III), GRN1005 (paclitaxel angiopep-2 peptide drug conjugate) or a mixture thereof.

3. The method according to claim 2 wherein said taxane is paclitaxel, docetaxel or a mixture thereof.

4. The method according to 1 wherein said lithium is lithium carbonate or lithium chloride.

5. The method according to claim 2 wherein said lithium is lithium carbonate or lithium chloride.

6. The method according to claim 3 wherein said lithium is lithium carbonate or lithium chloride.

7. A method of treatment comprising inhibiting, reducing the likelihood of onset of or ameliorating central nervous system effects of reduced cognition/cognitive impairment in a patient in need caused by the administration of an anti-cancer active agent by co-administering to the patient a pharmaceutically effective amount of lithium, wherein the anti-cancer active agent is a taxane, a *vinca* alkaloid or a mixture thereof, and wherein the lithium is co-administered to the patient between one to four hours prior to the administration of the anti-cancer active agent.

8. The method according to claim 7 wherein said taxane is selected from the group consisting of paclitaxel, docetaxel, IDN 5390 (13-(N-Boc-3-i-butylisoserinoyl)-C-7,8-seco-10-deacetylbaccatin III), GRN1005 (paclitaxel angiopep-2 peptide drug conjugate) or a mixture thereof.

9. The method according to claim 8 wherein said taxane is paclitaxel, docetaxel or a mixture thereof.

10. The method according to claim 7 wherein said lithium is lithium carbonate or lithium chloride.

11. The method according to claim 8 wherein said lithium is lithium carbonate or lithium chloride.

12. The method according to claim 9 wherein said lithium is lithium carbonate or lithium chloride.

13. A method of treatment comprising inhibiting, reducing the likelihood of onset of or ameliorating neuropathy in a patient in need caused by the administration of an anti-cancer active agent by co-administering to the patient a pharmaceutically effective amount of lithium, wherein the anti-cancer active agent is a taxane, a *vinca* alkaloid or a mixture thereof, and wherein the lithium is co-administered to the patient between one to four hours prior to the administration of the anti-cancer active agent.

14. The method according to claim 13 wherein said taxane is selected from the group consisting of paclitaxel, docetaxel, IDN 5390 (13-(N-Boc-3-i-butylisoserinoyl)-C-7,8-seco-10-deacetylbaccatin III), GRN1005 (paclitaxel angiopep-2 peptide drug conjugate) or a mixture thereof.

15. The method according to claim 14 wherein said taxane is paclitaxel, docetaxel or a mixture thereof.

16. The method according to claim 13 wherein said lithium is lithium carbonate or lithium chloride.

17. The method according to claim 14 wherein said lithium is lithium carbonate or lithium chloride.

18. The method according to claim 15 wherein said lithium is lithium carbonate or lithium chloride.

* * * * *